(12) United States Patent
Chung et al.

(10) Patent No.: US 9,181,542 B2
(45) Date of Patent: Nov. 10, 2015

(54) METHOD FOR CONTROLLING THE CHAPERONE ACTIVITY OF PEROXIREDOXINS USING IRRADIATION

(75) Inventors: Byung Yeoup Chung, Jeollabuk-do (KR); Seung Sik Lee, Jeollabuk-do (KR); Byung Chull An, Gyeongsangnam-do (KR); Eun Mi Lee, Jeollabuk-do (KR); Jae Taek Lee, Jeollabuk-do (KR); Hyoung-Woo Bai, Jeollabuk-do (KR)

(73) Assignee: Korea Atomic Energy Research Institute, Daejeon (KR)

( * ) Notice: Subject to any disclaimer, the term of this patent is extended or adjusted under 35 U.S.C. 154(b) by 0 days.

(21) Appl. No.: 13/881,017

(22) PCT Filed: Oct. 25, 2011

(86) PCT No.: PCT/KR2011/007998
§ 371 (c)(1),
(2), (4) Date: Apr. 23, 2013

(87) PCT Pub. No.: WO2012/057508
PCT Pub. Date: May 3, 2012

(65) Prior Publication Data
US 2013/0210108 A1    Aug. 15, 2013

(30) Foreign Application Priority Data

Oct. 25, 2010  (KR) .................. 10-2010-0103847
Oct. 25, 2011  (KR) .................. 10-2011-0109331

(51) Int. Cl.
*C12N 13/00* (2006.01)
*C12N 9/04* (2006.01)

(52) U.S. Cl.
CPC .............. *C12N 13/00* (2013.01); *C12N 9/0006* (2013.01); *C12Y 111/01015* (2013.01)

(58) Field of Classification Search
CPC ................................................ C12Y 111/01015
See application file for complete search history.

(56) References Cited

U.S. PATENT DOCUMENTS

2006/0147440 A1*  7/2006  Fesenko et al. .............. 424/94.4

FOREIGN PATENT DOCUMENTS

WO   PCT/KR2011/007998    5/2012

OTHER PUBLICATIONS

Caillet et al. ("Effect of gamma radiation on hear shock protein expression of four foodborne pathogens", Journal of Applied Microbiology, 2008, pp. 1384-1391).*

An et al. ("A New Antioxidant with Dual Functions as a Peroxidase and Chaperone in Pseudomonas aeruginosa", Molecules and Cells, Feb. 28, 2010; published online Jan. 12, 2010; pp. 141-151).*
An et al. (FI-09—The Functional Change in Enzymatic dual Function of Peroxiredoxin Protein by Gamma Ray, document pp. 1-5; presented at the International Meeting on Radiation Processing (IMRP), Montreal, Wisconsin, Jun. 2011).*
US EPA, "Gamma Rays", pp. 1-5 obtained from http://www.epa.gov/radiation/understand/gamma.*
Moon et al., "Oxidative Stress-dependent Structural and Functional Switching of a Human 2-Cys Peroxiredoxin Isotype II That Enhances HeLa Cell Resistance to H2O2-induced Cell Death", J. Biol. Chem, pp. 28775-28784, 2005.*
Woo et al., "Immunoblot Detection of Proteins That Contain Cysteine Sulfinic or Sulfonic Acids with Antibodies Specific for Hyperoxidized Cysteine-Containing Sequence", Methods in Redox Signaling, pp. 19-23, 2010.*
Markakis et al., "Products of g-Irradiation of Cysteine and Cystine", J. Am. Chem. Soc., pp. 1613-1617, 1960.*
Manta et al., "The peroxidase and peroxynitrite reductase activity of human erythrocyte peroxiredoxin 2", Archives of Biochemistry and Biophysics, 2009, pp. 146-154.*
Solar and Sustainable Energy; https://ag.tennessee.edu/solar/Pages/What%20Is%20Solar%20Energy/Sunlight.aspx; obtained Jul. 10, 2015; p. 1.*
Jang et al., "Phosphorylation and Concomitant Structural Changes in Human 2-Cys Peroxiredoxin Isotype I Differentially Regulate its Peroxidase and Molecular Chaperone Functions" FEBS Letters 2006 580:351-355.
Lee et al., "Differential Expression of Prx I and II in Mouse Testis and Their Up-Regulation by Radiation" Biochemical and Biophysical Research Communications 2002 296:337-342.
Zhang et al., "Differentially Expressed Proteins of Gamma-Ray Irradiated Mouse Intestinal Epithelial Cells by Two-Dimensional Electrophoresis and MALDI-TOF Mass Spectrometry" World Journal of Gastroenterology 2003 9 (12):2726-2731.
Chull et al., "A New Antioxidant with Dual Functions as a Peroxidase and Chaperon in *Pseudomonas aeroginosa*" Molecules and Cells 2010 29:145-151.
Hishinuma et al., "OxyR Regulated the Expression of Two Major Catalases, KatA and KatB, along with Peroxiredoxin, AhpC in *Pseudomonas putida*" Environmental Microbioogy 2006 8(12):2115-2124.

* cited by examiner

*Primary Examiner* — Karlheinz R Skowronek
*Assistant Examiner* — Lianko Garyu
(74) *Attorney, Agent, or Firm* — Licata & Tyrrell P.C.

(57) ABSTRACT

The present invention relates to a method for increasing chaperone activity by irradiating peroxiredoxin (Prx) proteins. More particularly, the present invention may be useful for preparing recombinant proteins imparting resistance against various environmental stresses by increasing the chaperone activity of peroxiredoxin, since it has been observed that irradiated peroxiredoxin has enhanced chaperone activity characteristics, wherein an α-helix structure decreases while a β-sheet structure increases, from analysis results of a protein structure change and chaperone activity after irradiating two types of peroxiredoxins (2-Cys, 3-Cys) which are two active cysteine motifs of peroxiredoxin.

4 Claims, 22 Drawing Sheets

[Fig. 1]
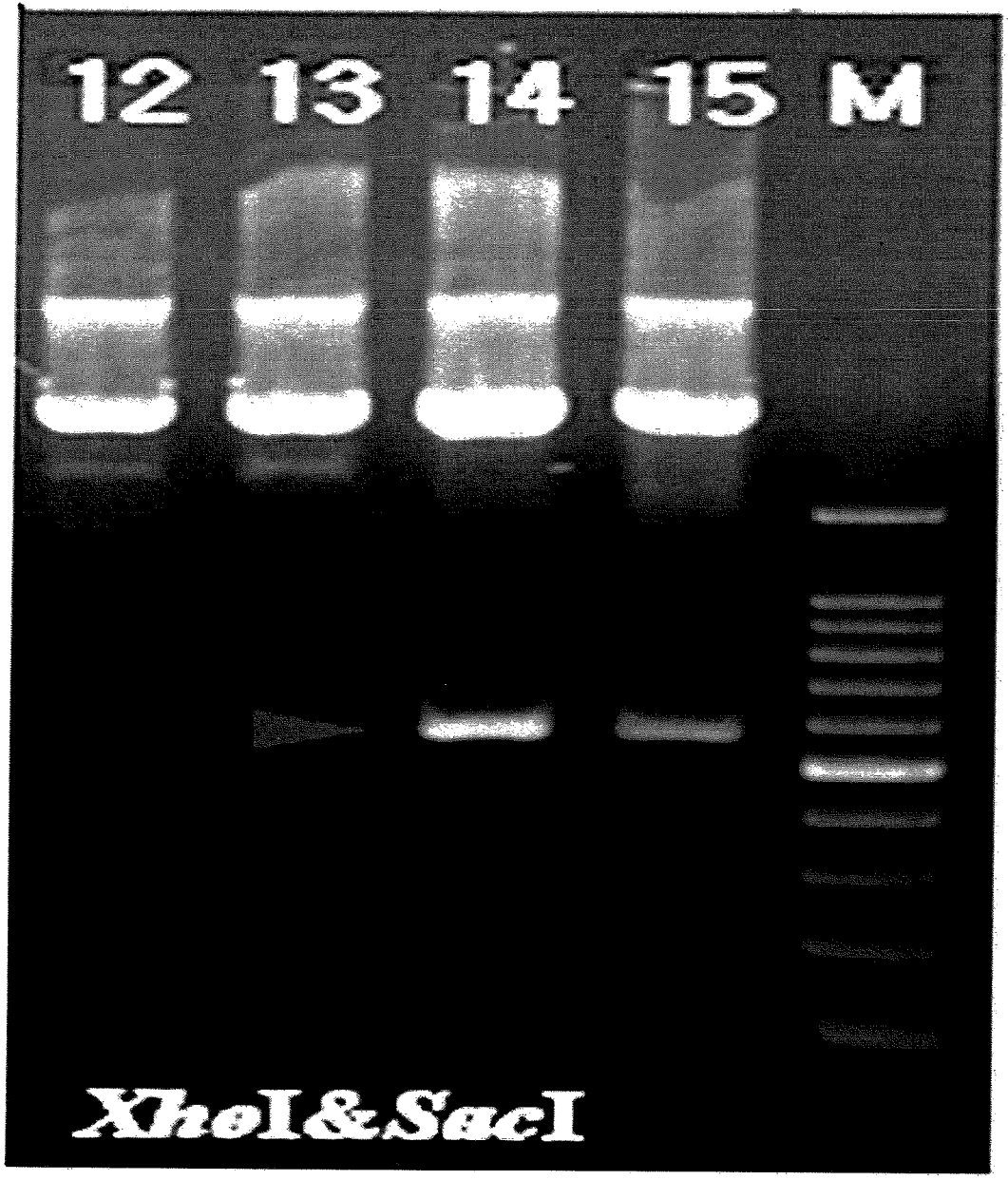
The subcloning of *PP1084 (3-Cys)* gene into the expression vector *pRSETa*
M: marker; and
12 ~ 15: *pRSETa::PP1084 (3-Cys)*

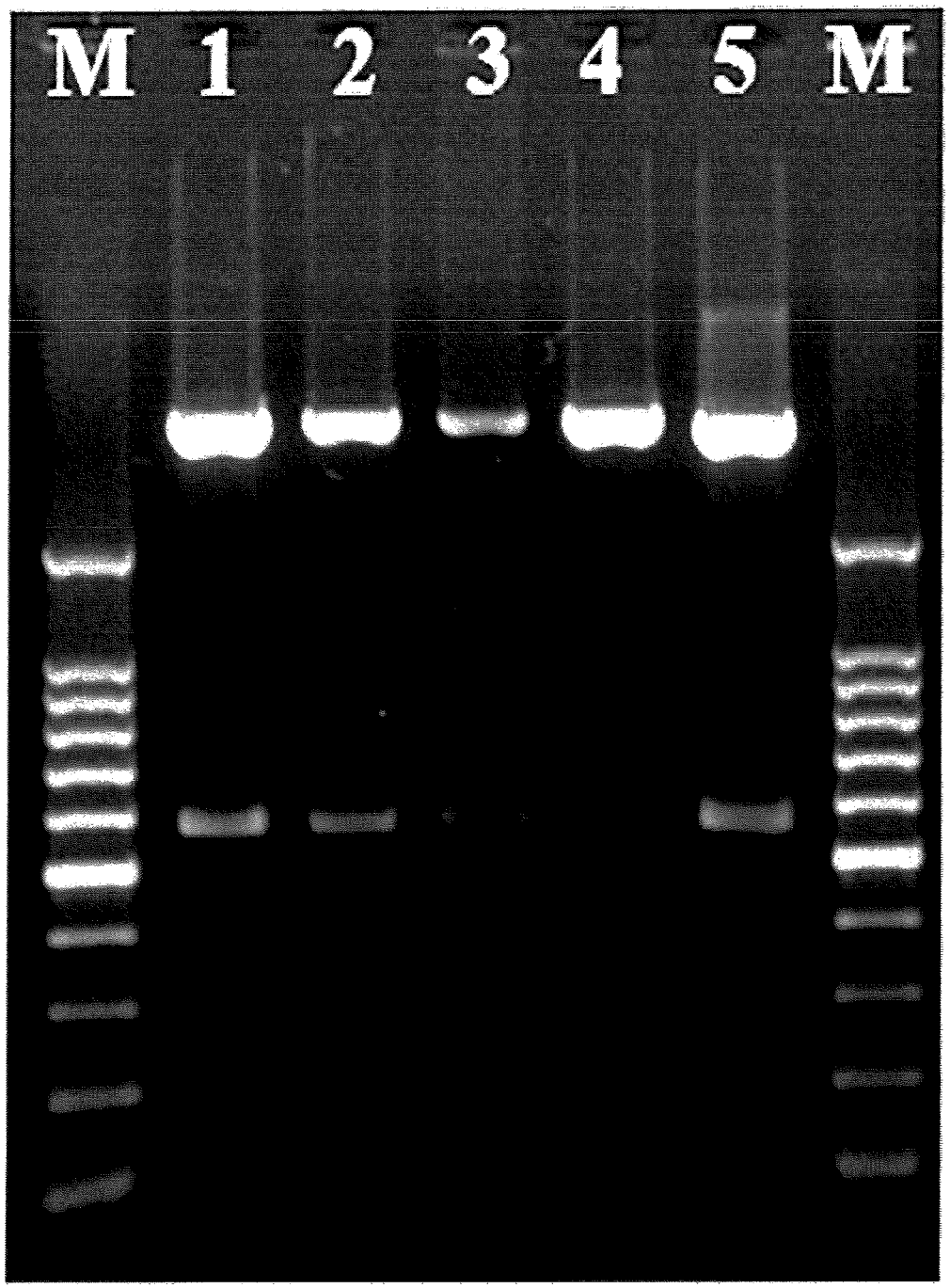
[Fig. 2]
The subcloning of *PA3529 (2-Cys)* gene into the expression vector *pRSETa*
M: marker; and
1 ~ 5: *pRSETa::PA3529 (2-Cys)*

[Fig. 3]
The confirming the expression of PP1084 protein in *E. Coli* (KRX)
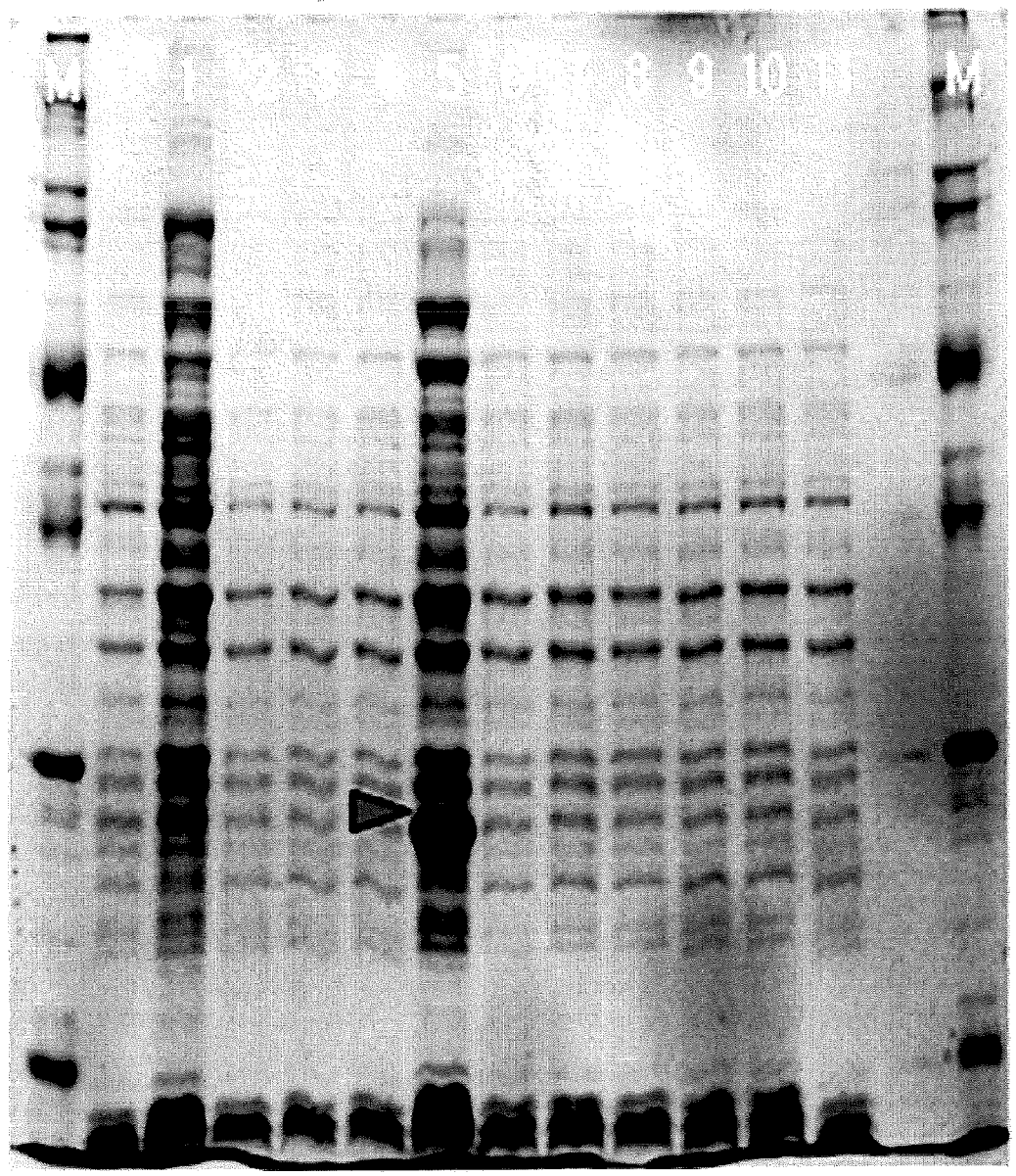

[Fig. 4]
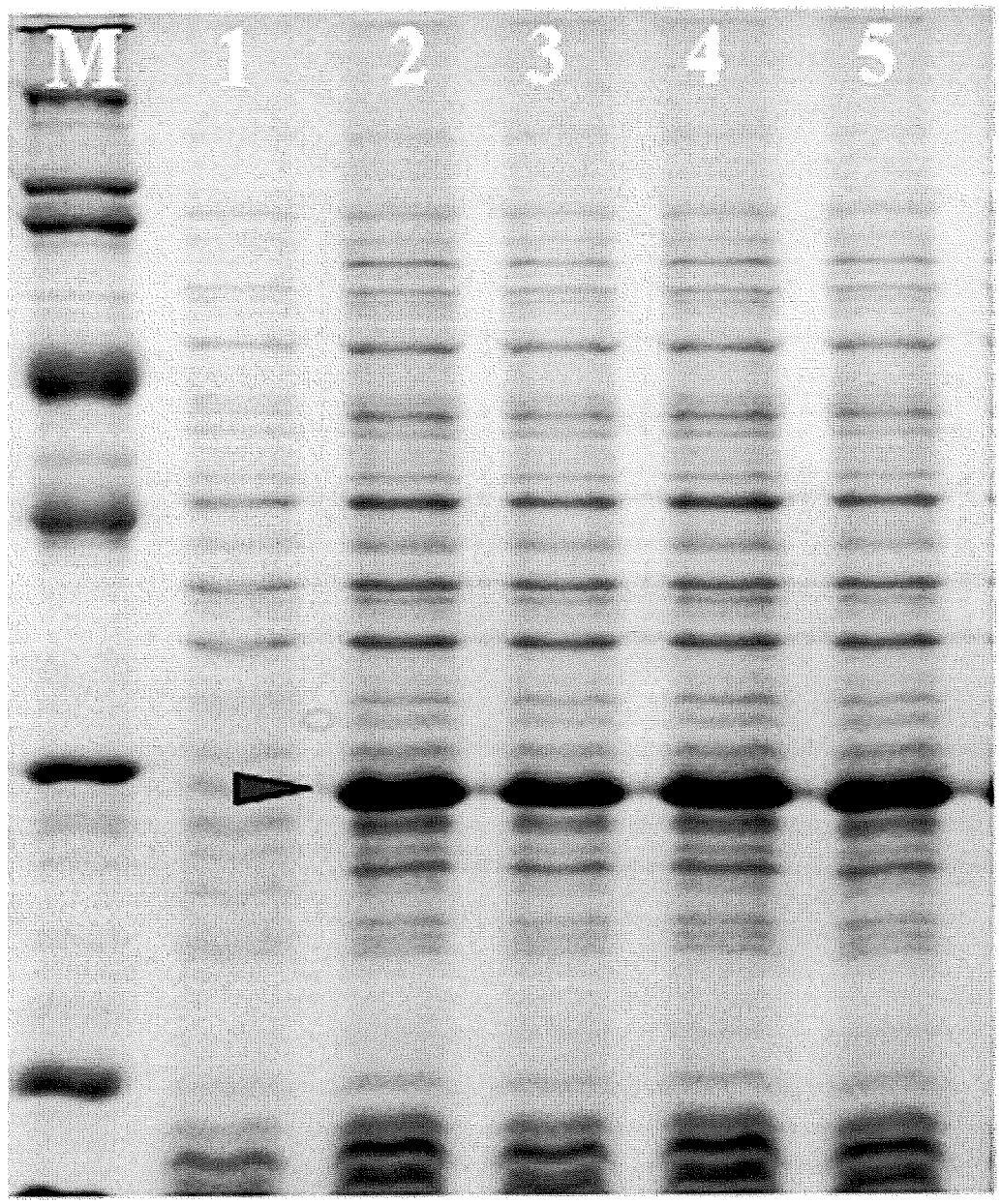

[Fig. 5]
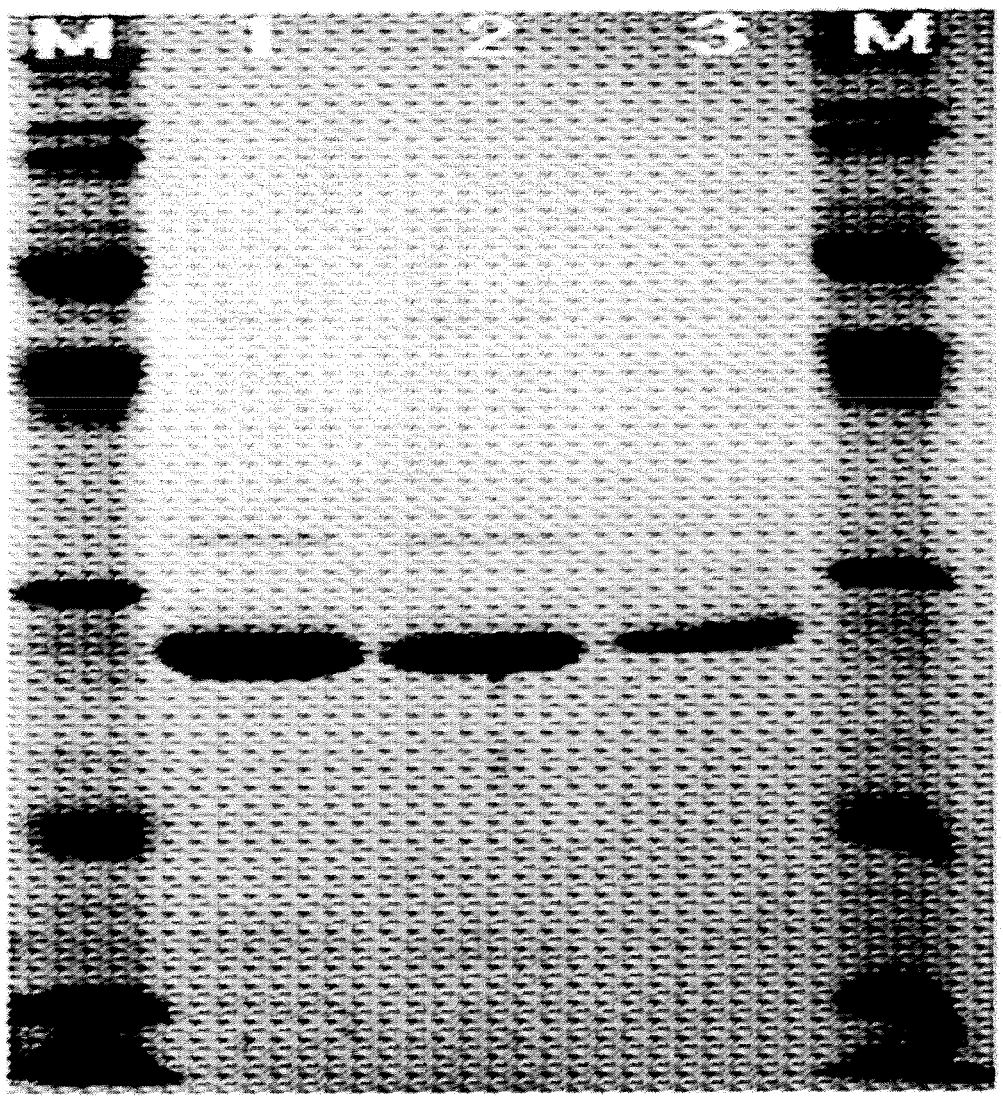
M: marker;
1: fraction 1;
2: fraction 2; and
3: fraction 3.

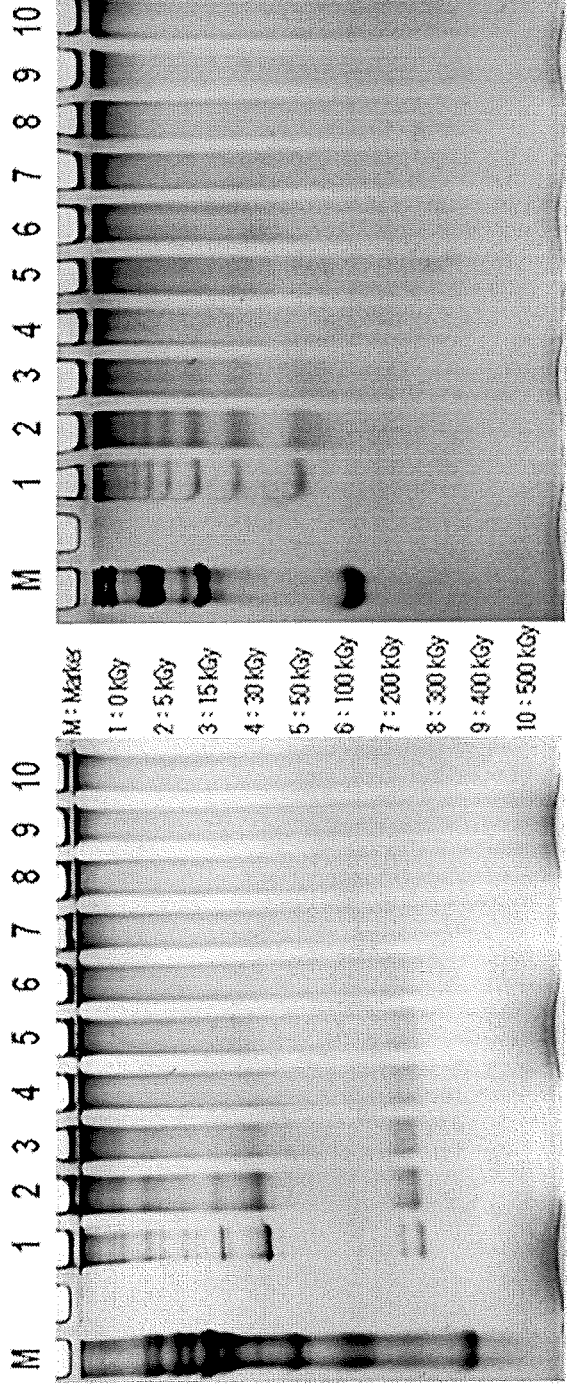
[Fig.6]
The illustrating the structural changes of PP1084 protein induced by irradiation with gamma ray, confirmed by loading on polyacrylamide gel

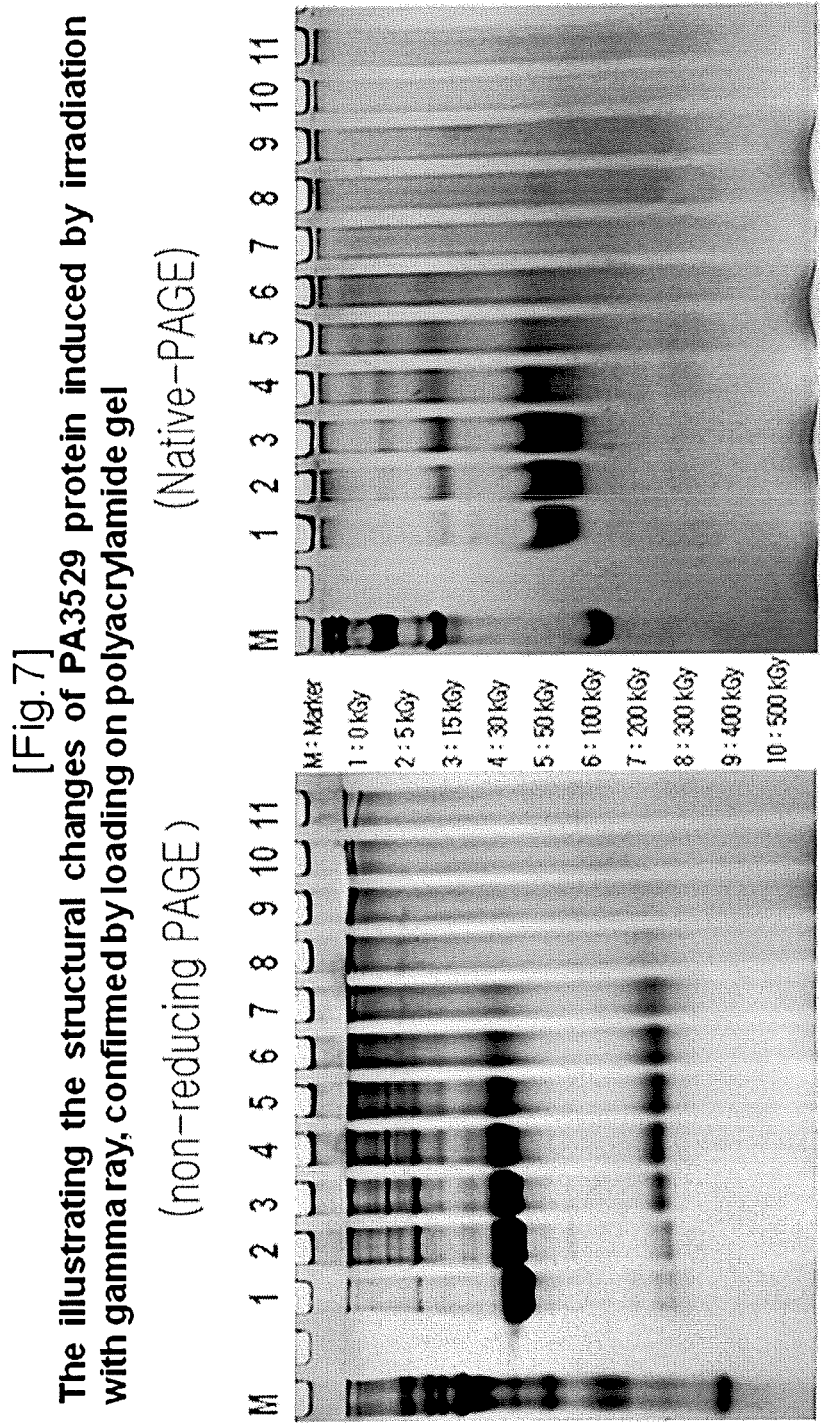
[Fig.7]
The illustrating the structural changes of PA3529 protein induced by irradiation with gamma ray, confirmed by loading on polyacrylamide gel

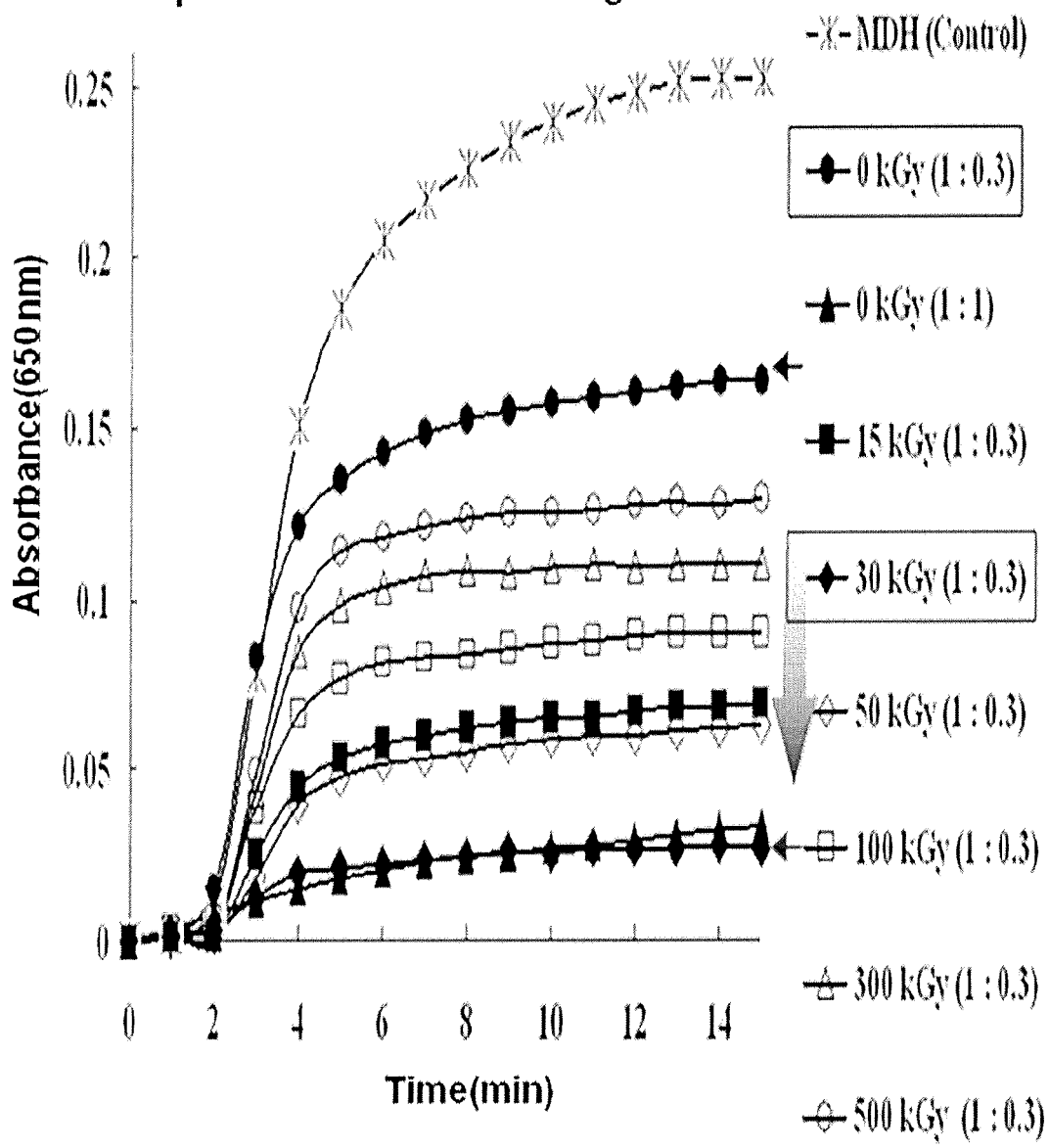

[Fig. 9]
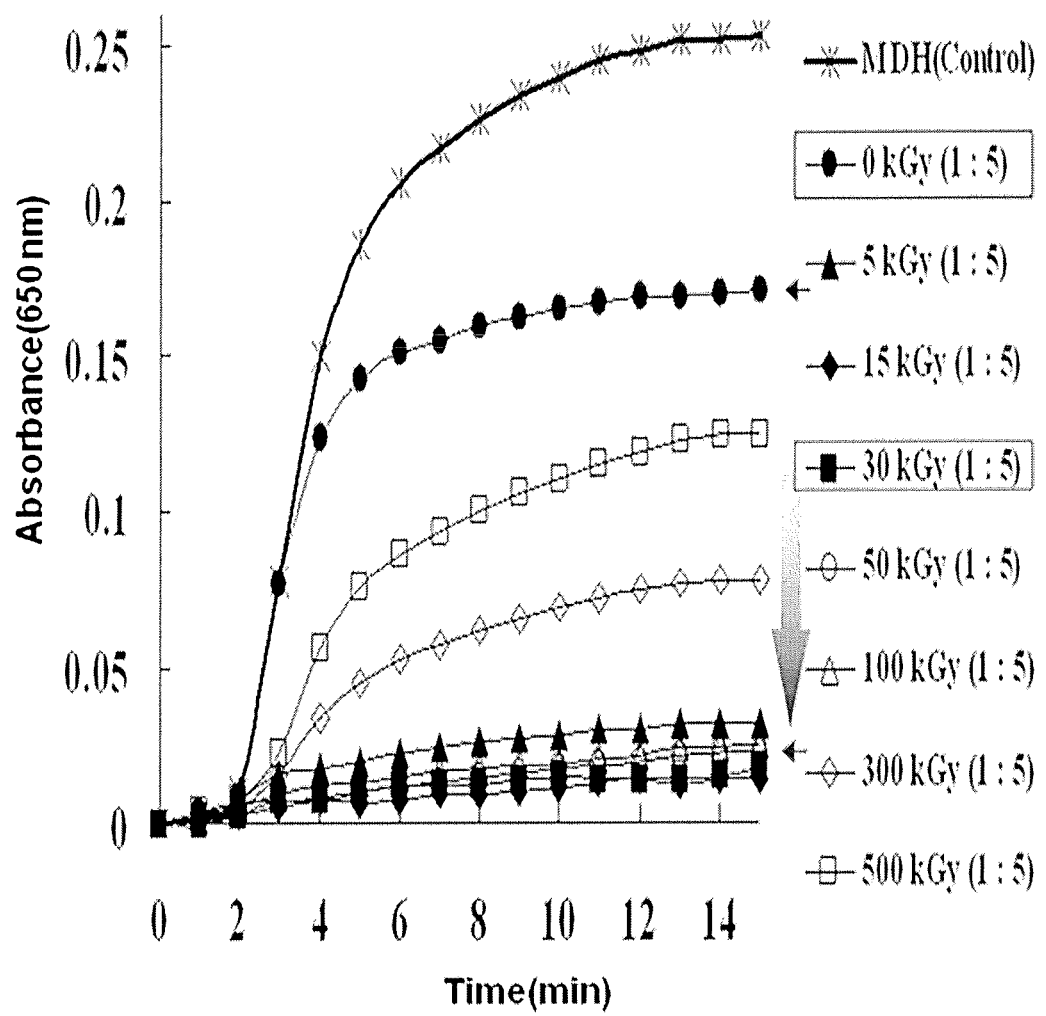

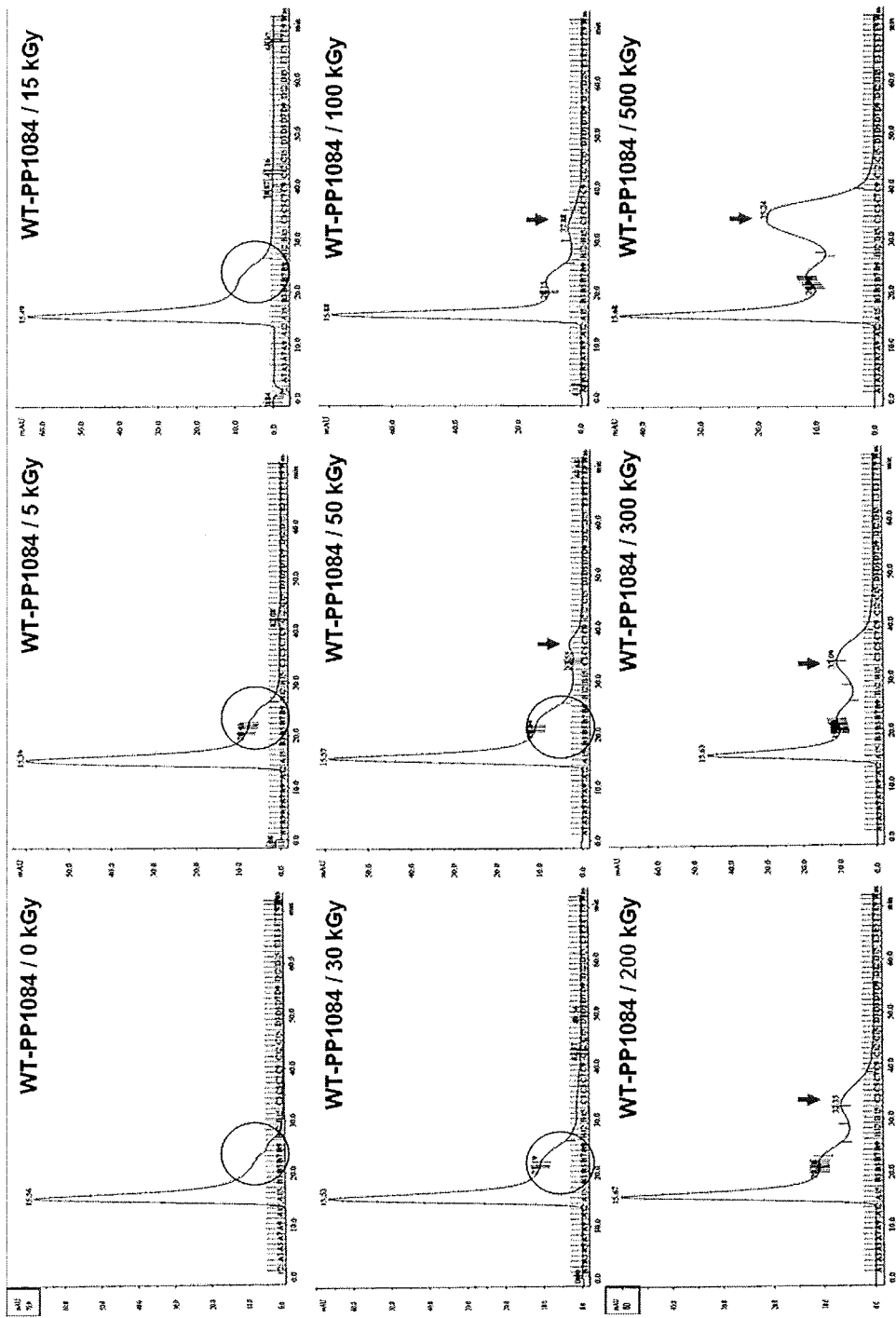
[Fig. 10]

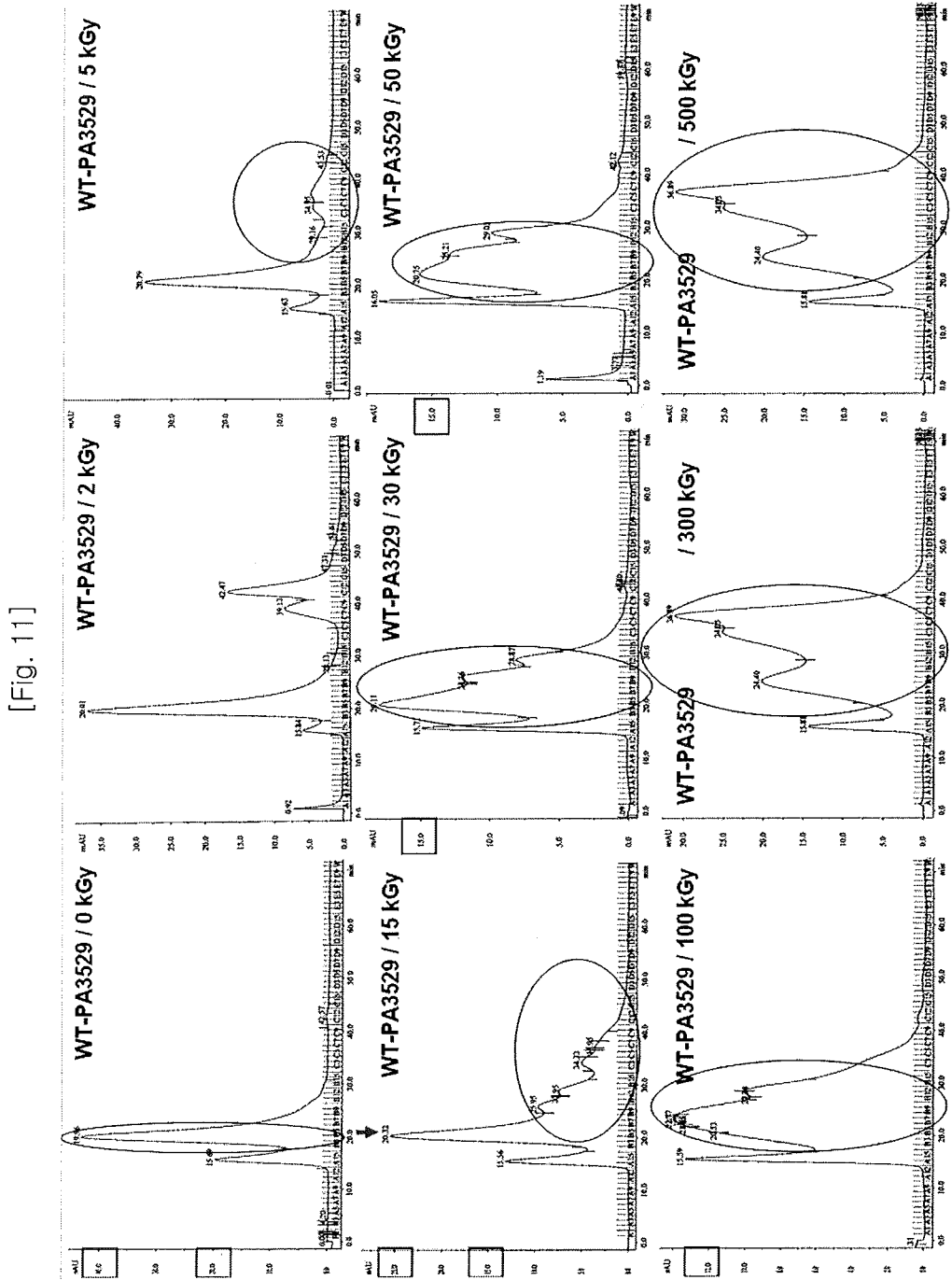
[Fig. 11]

[Fig. 12]
The partial structural changes of PP1084 protein induced by high dose gamma irradiation
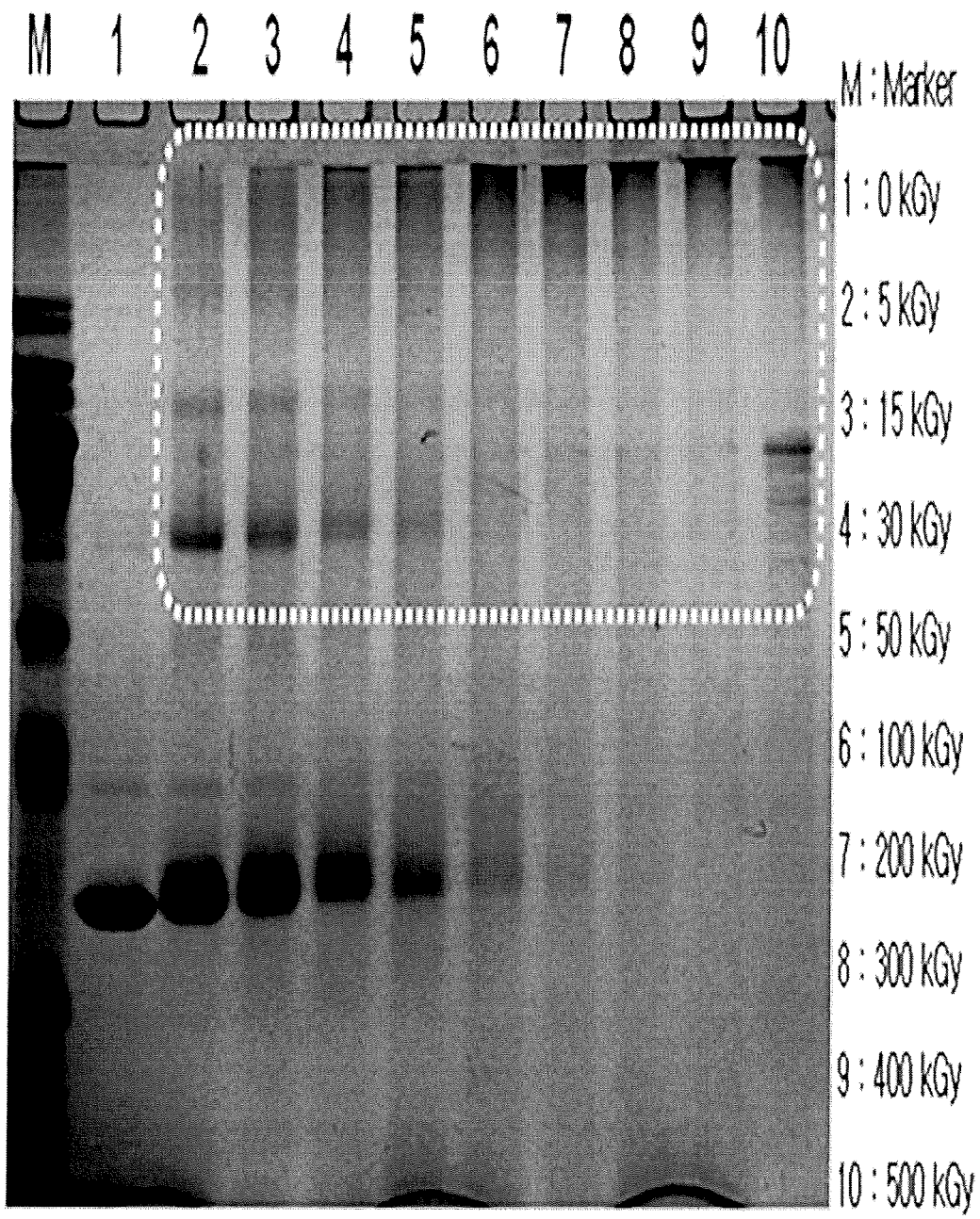

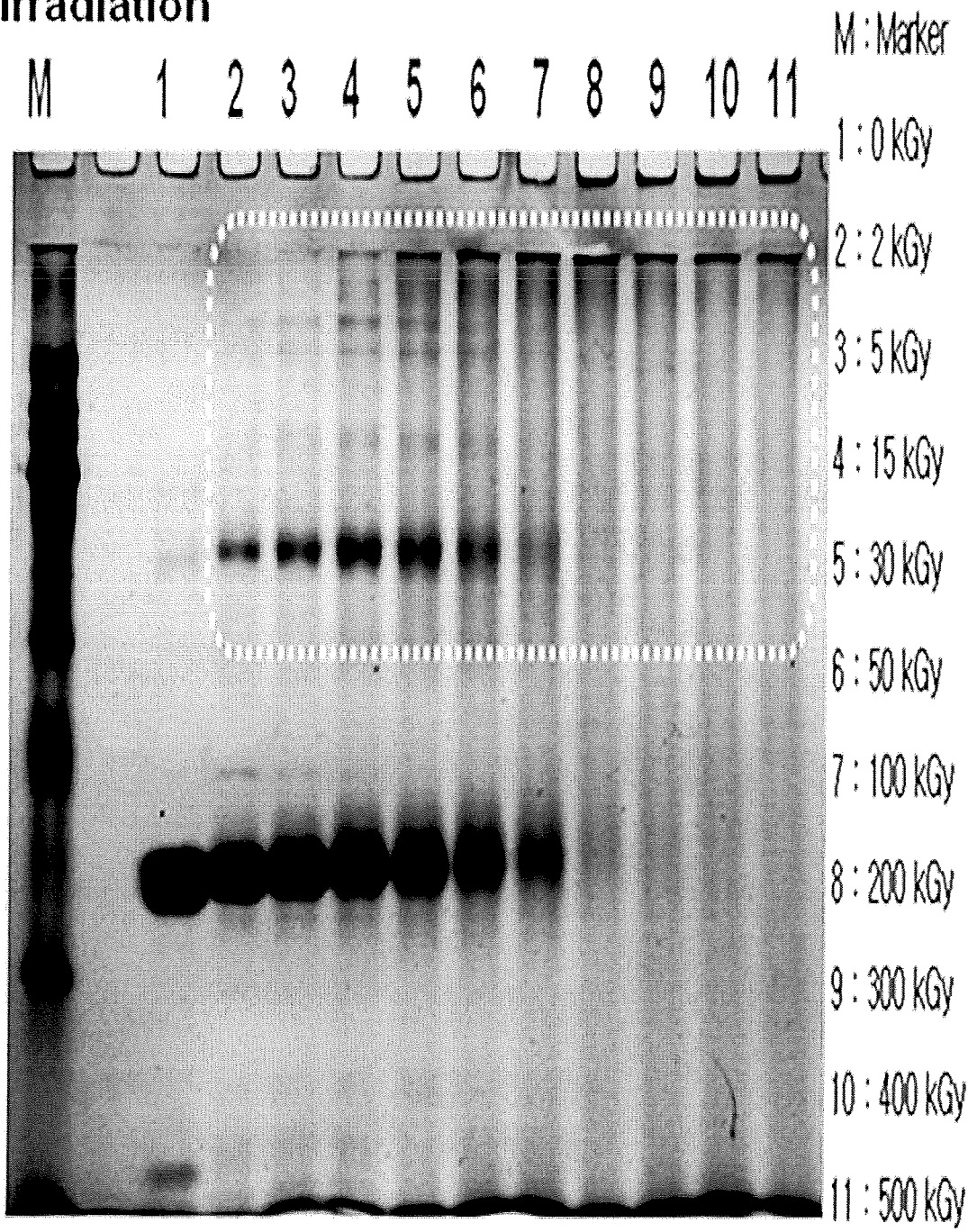
[Fig. 13]
The partial structural changes of PA 3529 protein induced by high dose gamma irradiation

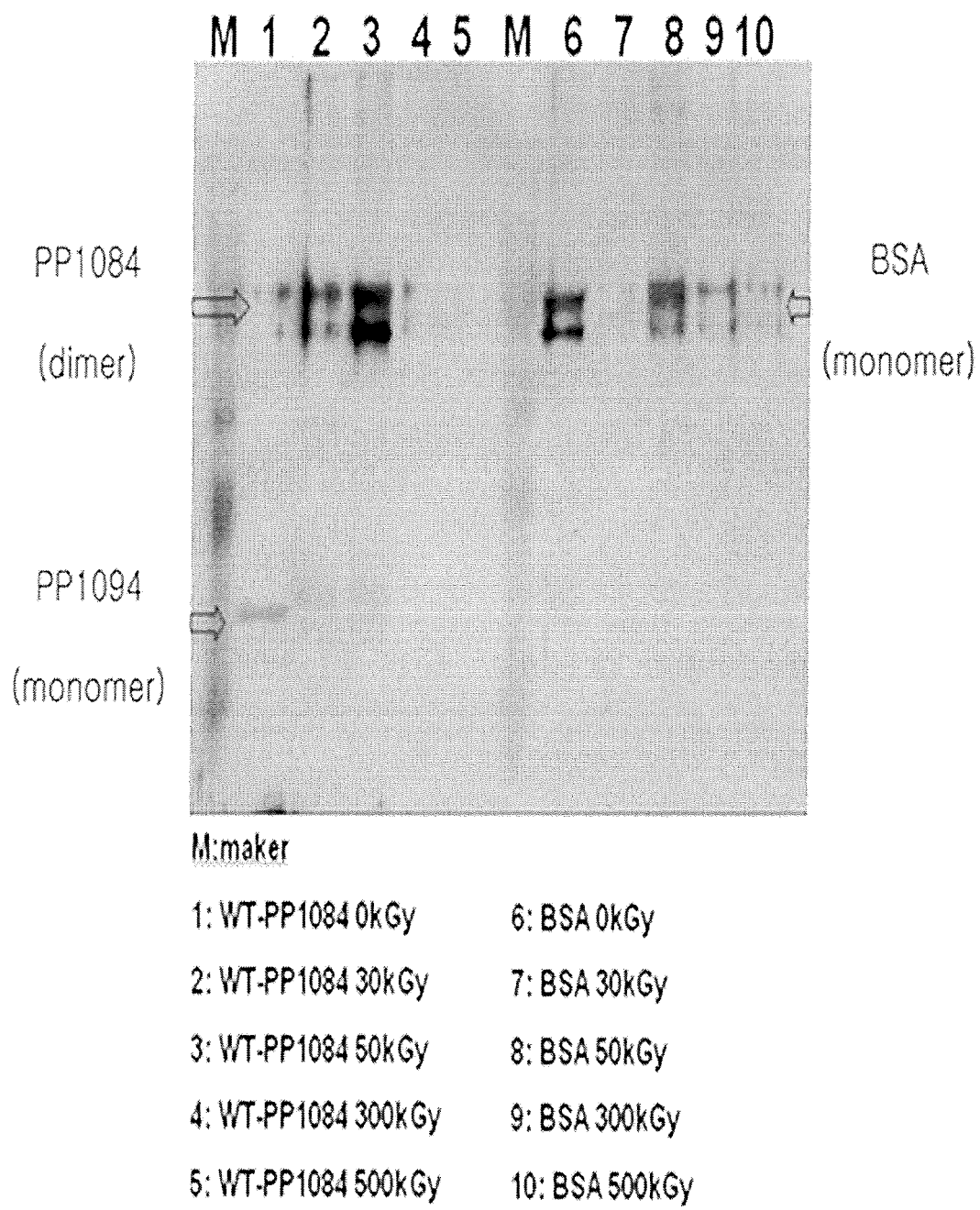

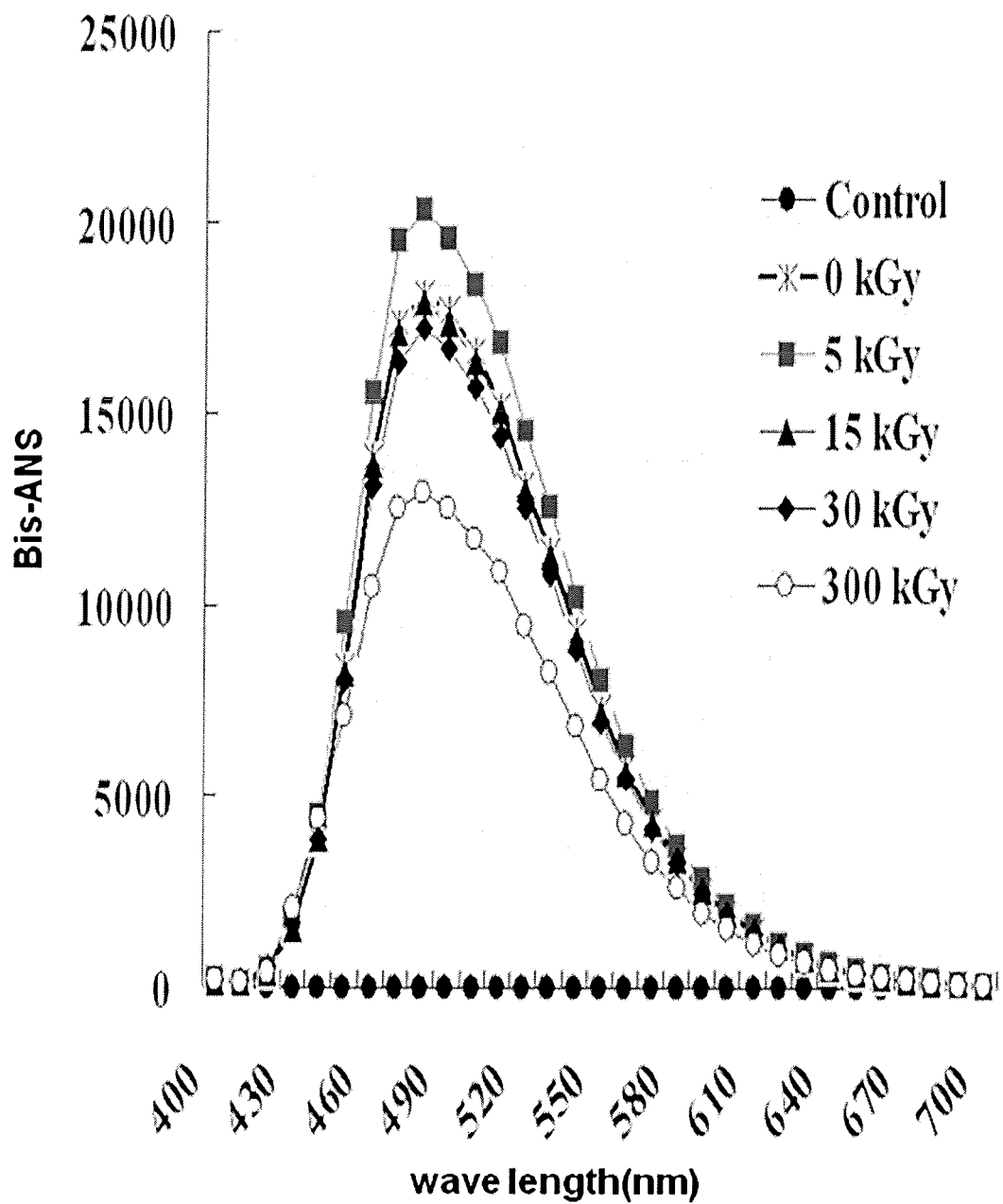
[Fig. 15]

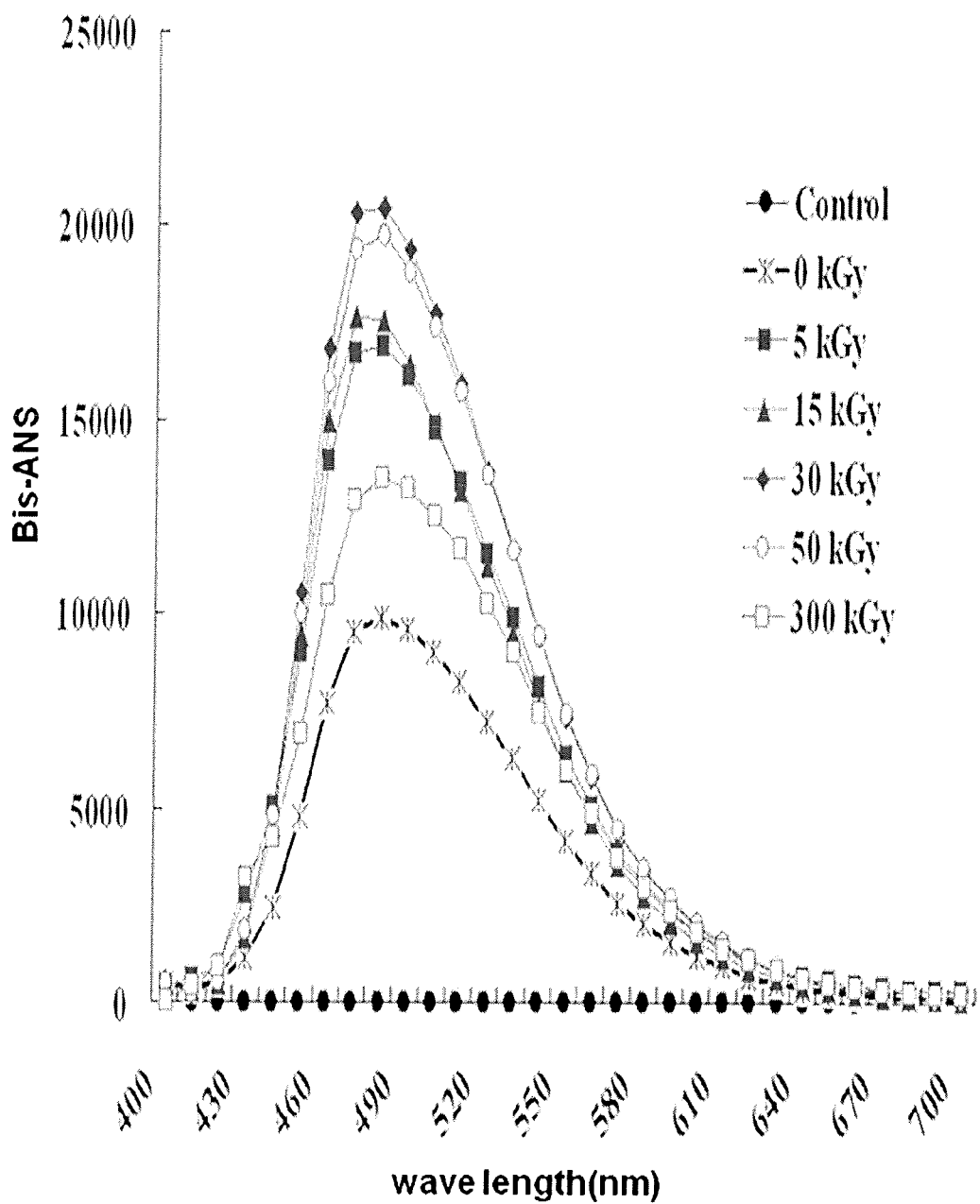
[Fig. 16]

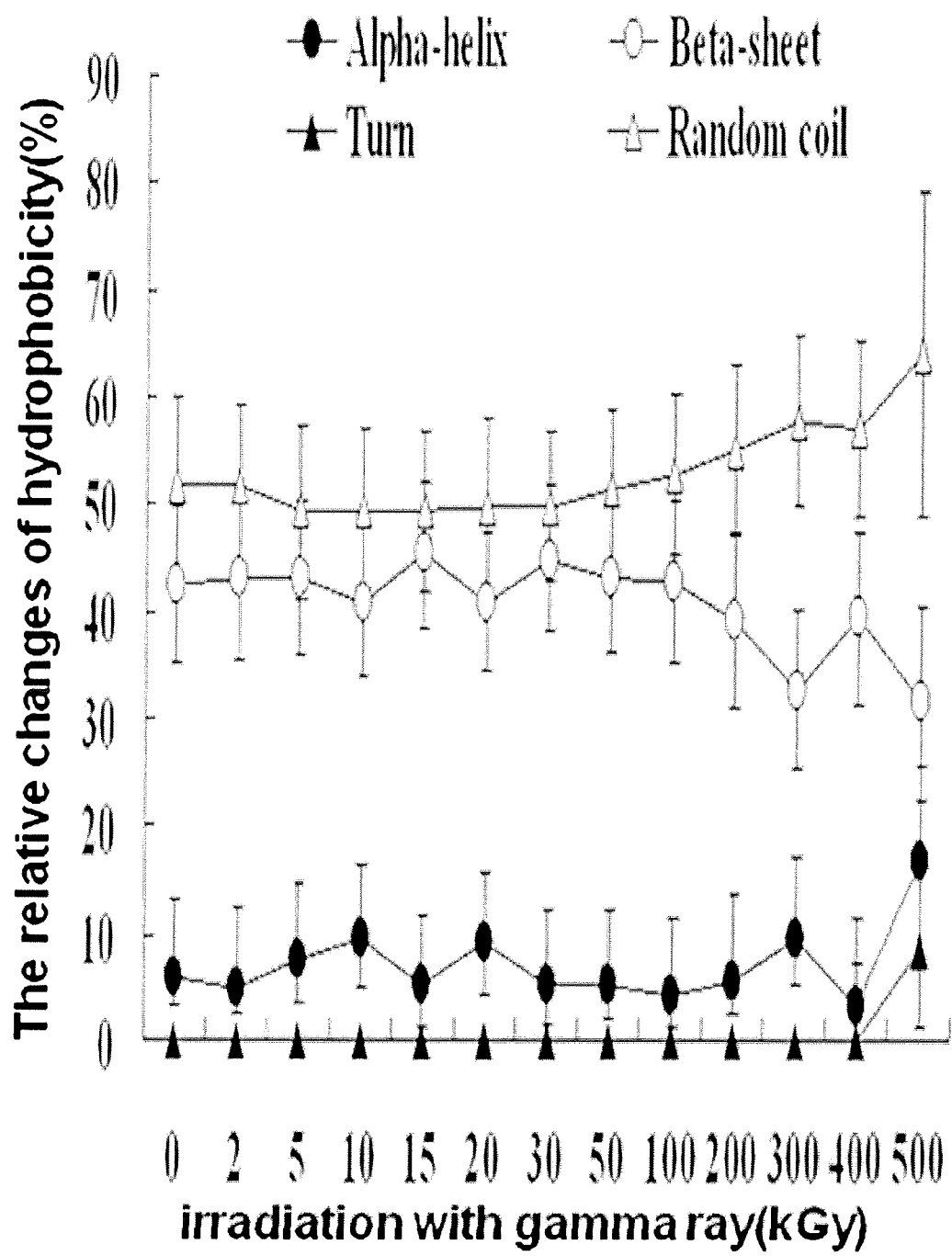
[Fig. 17]

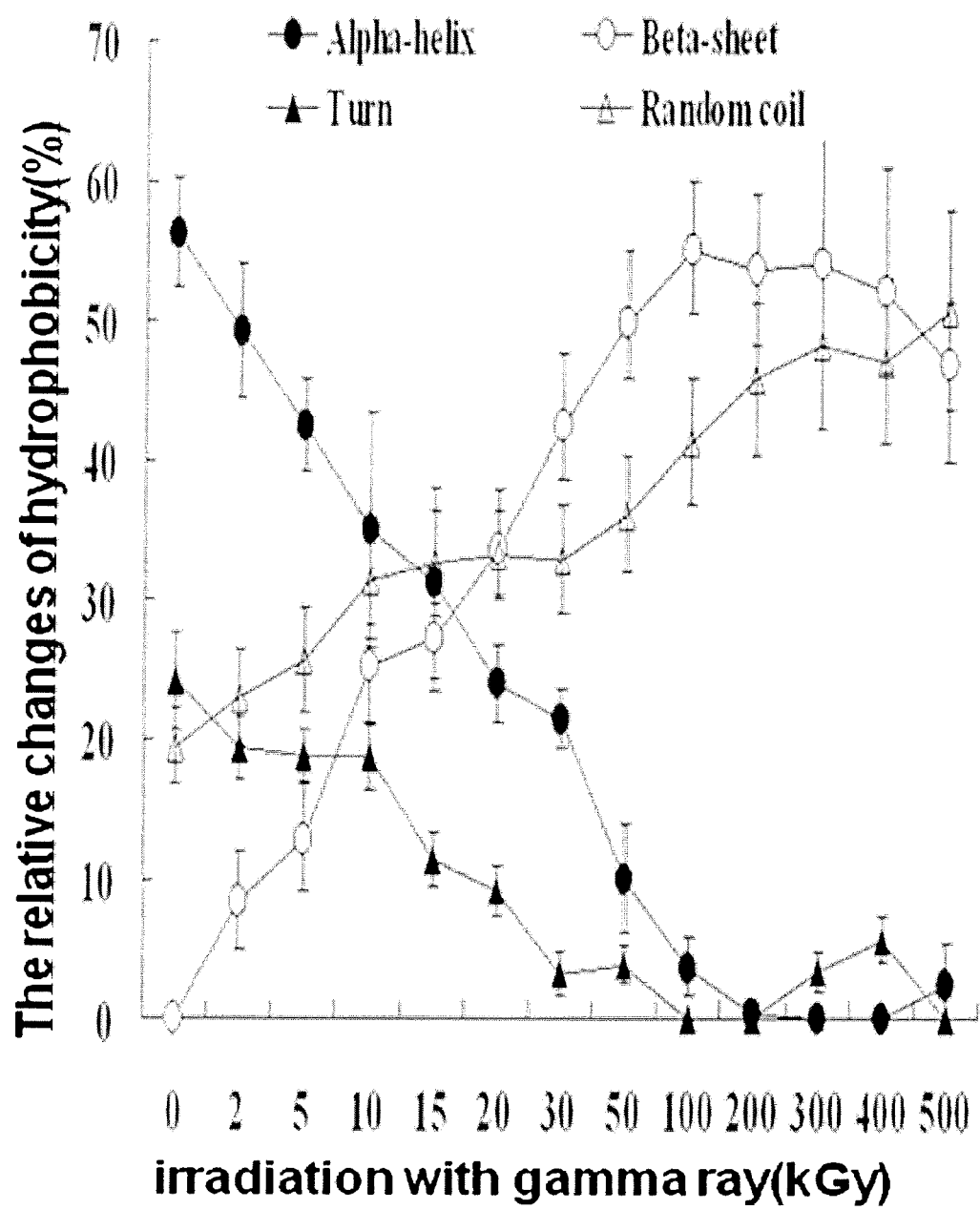
[Fig. 18]

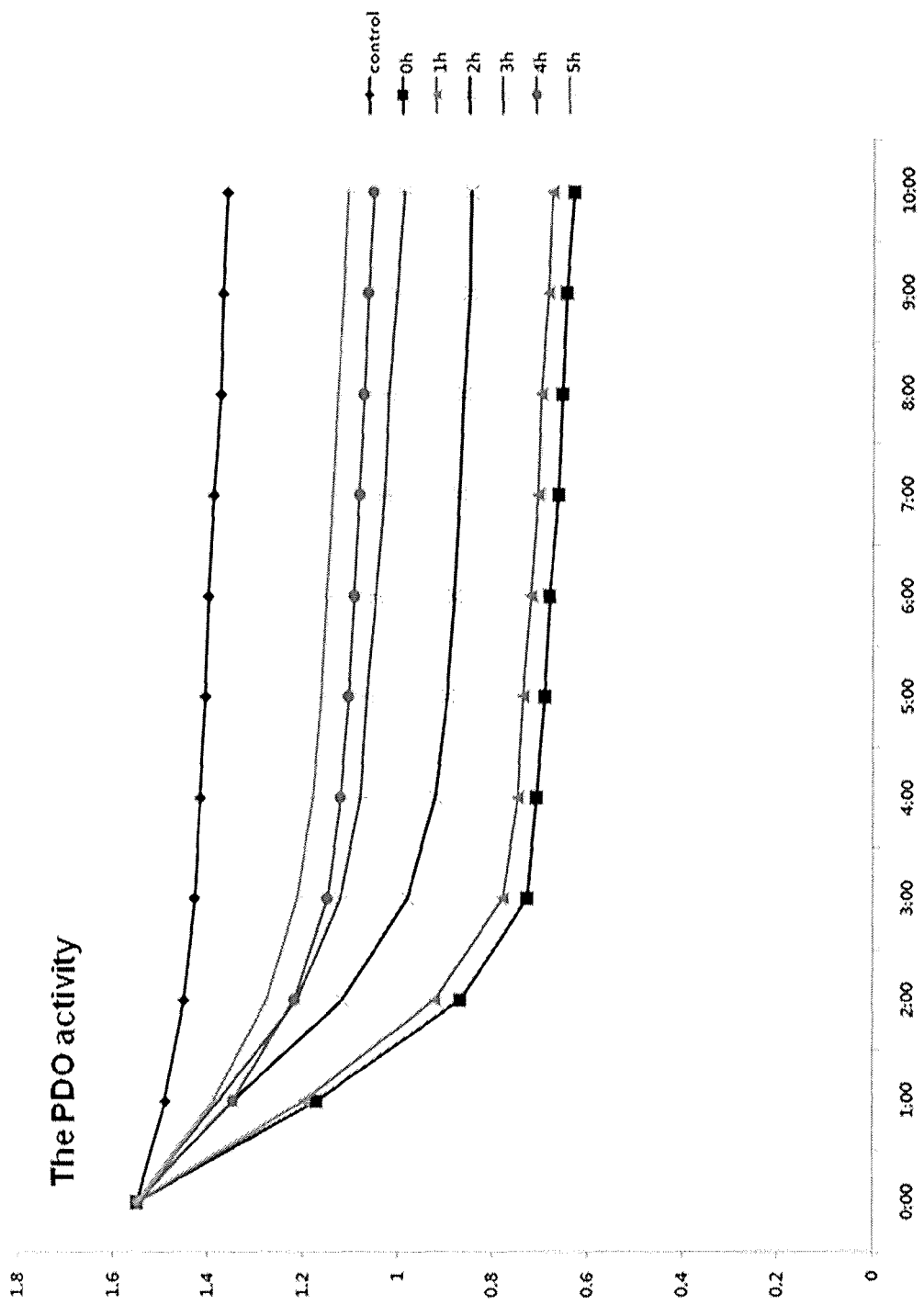
[Fig. 20]

[Fig. 21]
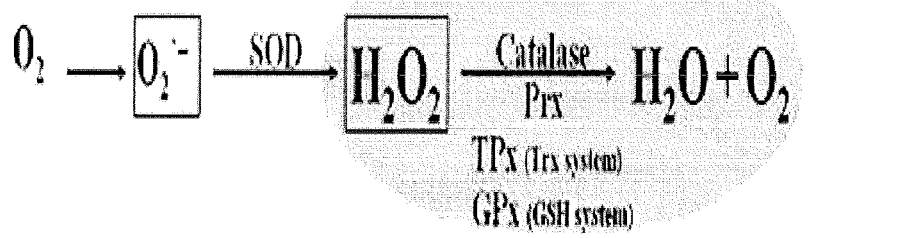
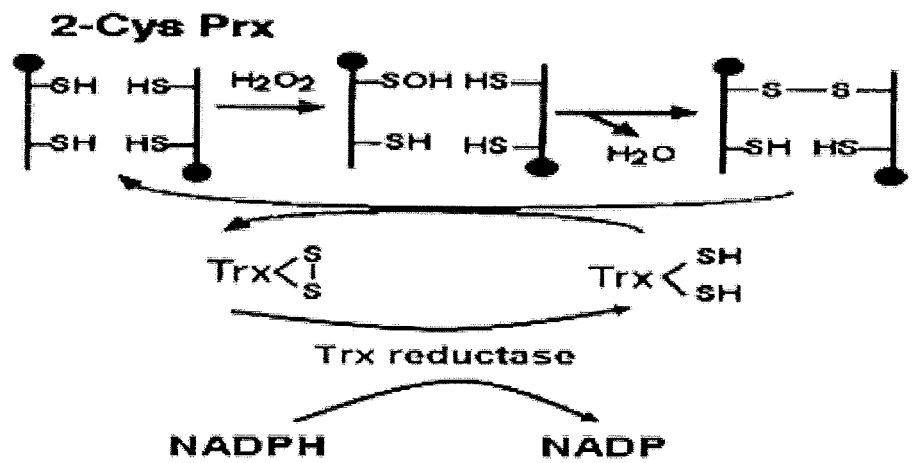
[Fig. 22]
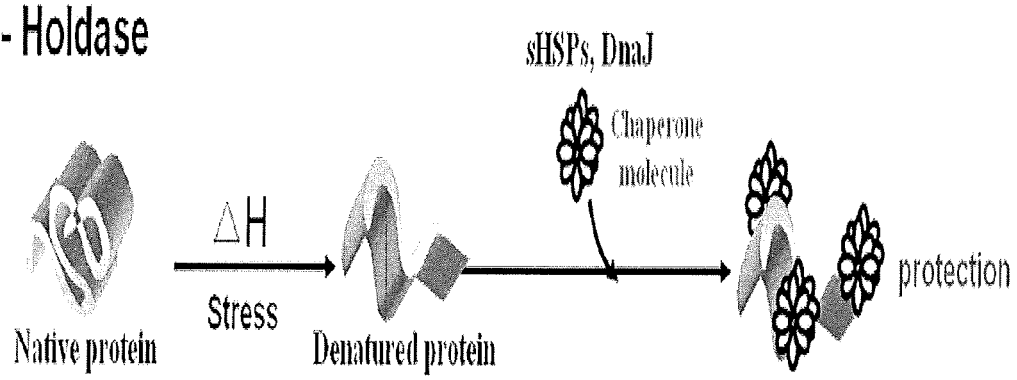

[Fig. 23]
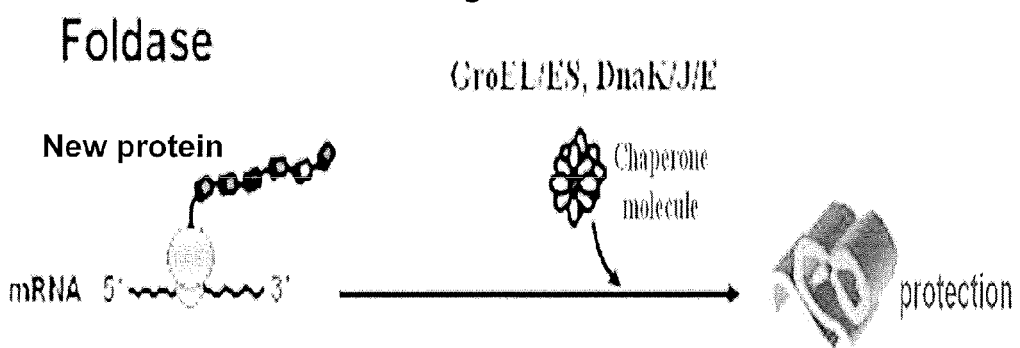

SEQUENCE LISTING

```
<160> NUMBER OF SEQ ID NOS: 6

<210> SEQ ID NO 1
<211> LENGTH: 200
<212> TYPE: PRT
<213> ORGANISM: Artificial Sequence
<220> FEATURE:
<223> OTHER INFORMATION: Two-Cys Peroxiredoxin Artificial Sequence

<400> SEQUENCE: 1
```

```
Met Ser Val Leu Val Gly Lys Lys Ala Pro Asp Phe Asn Val Ala Ala
1               5                   10                  15

Val Leu Gly Asn Gly Glu Ile Val Glu Ser Phe Thr Leu Ser Glu Ala
                20                  25                  30

Ile Lys Gly Lys Tyr Gly Leu Val Phe Phe Tyr Pro Leu Asp Phe Thr
                35                  40                  45

Phe Val Cys Pro Ser Glu Leu Ile Ala Leu Asp His Arg Ile Pro Glu
        50                  55                  60

Phe Gln Ala Arg Asn Val Glu Val Ile Gly Val Ser Ile Asp Ser His
65                  70                  75                  80

Phe Thr His Asn Ala Trp Arg Asn Thr Pro Val Asp Lys Gly Gly Ile
                85                  90                  95

Gly Ala Val Lys Tyr Thr Leu Ala Ala Asp Thr Lys His Glu Ile Ala
                100                 105                 110

Lys Ala Tyr Asp Val Glu Ser Asp Gly Val Ala Phe Arg Gly Ala
                115                 120                 125

Phe Leu Ile Asp Lys Glu Gly Val Val Arg Ser Gln Ile Val Asn Asp
        130                 135                 140

Leu Pro Leu Gly Arg Asn Met Asp Glu Leu Leu Arg Leu Val Asp Ala
145                 150                 155                 160

Leu Gln Phe His Glu Glu His Gly Glu Val Cys Pro Ala Asn Trp Lys
                165                 170                 175

Lys Gly Asp Lys Gly Met Thr Ala Ser Pro Glu Gly Val Ala Lys Tyr
                180                 185                 190

Leu Ala Glu Asn Ala Ser Lys Leu
        195                 200

<210> SEQ ID NO 2
<211> LENGTH: 200
<212> TYPE: PRT
<213> ORGANISM: Artificial Sequence
<220> FEATURE:
<223> OTHER INFORMATION: Three-Cys Peroxiredoxin
      Artificial Sequence

<400> SEQUENCE: 2

Met Ser Val Leu Val Gly Lys Lys Ala Pro Asp Phe Thr Val Pro Ala
1               5                   10                  15

Val Leu Gly Asn Gly Glu Ile Val Asp Ser Phe Asn Leu Ala Ser Ala
                20                  25                  30

Ile Lys Gly Lys Tyr Gly Leu Val Phe Phe Tyr Pro Leu Asp Phe Thr
                35                  40                  45

Phe Val Cys Pro Ser Glu Leu Ile Ala Leu Asp Asn Arg Ile Pro Asp
        50                  55                  60

Phe Gln Ala Arg Asn Val Glu Val Ile Gly Val Ser Ile Asp Ser His
65                  70                  75                  80

Phe Thr His Asn Ala Trp Arg Asn Thr Pro Val Asn Asn Gly Gly Ile
                85                  90                  95

Gly Gln Val Lys Tyr Thr Leu Ala Ala Asp Met Thr His Glu Ile Cys
                100                 105                 110

Lys Ala Tyr Asp Val Glu Ser Glu Gly Val Ala Phe Arg Gly Ala
                115                 120                 125

Phe Leu Ile Asp Thr Asn Gly Val Val Arg Ser Gln Ile Val Asn Asp
        130                 135                 140

Leu Pro Leu Gly Arg Asn Met Asp Glu Leu Leu Arg Leu Val Asp Ala
145                 150                 155                 160
```

```
Leu Gln Phe His Glu Glu His Gly Glu Val Cys Pro Ala Asn Trp Lys
                165             170                 175

Lys Gly Asp Lys Gly Met Asn Ala Ser Pro Glu Gly Val Ala Ala Tyr
            180                 185                 190

Leu Ser Glu Asn Ala Gly Lys Leu
        195                 200

<210> SEQ ID NO 3
<211> LENGTH: 21
<212> TYPE: DNA
<213> ORGANISM: Pseudomonas aeruginosa

<400> SEQUENCE: 3
ccgctcgaga tgagcgtact c                                             21

<210> SEQ ID NO 4
<211> LENGTH: 22
<212> TYPE: DNA
<213> ORGANISM: Pseudomonas aeruginosa

<400> SEQUENCE: 4
cgaccgttcg acattctcga gc                                            22

<210> SEQ ID NO 5
<211> LENGTH: 24
<212> TYPE: DNA
<213> ORGANISM: Pseudomonas putida

<400> SEQUENCE: 5
ccgctcgaga tgagcgtact cgta                                          24

<210> SEQ ID NO 6
<211> LENGTH: 24
<212> TYPE: DNA
<213> ORGANISM: Pseudomonas putida

<400> SEQUENCE: 6
cggtcgttcg acattttcga accc                                          24
```

METHOD FOR CONTROLLING THE CHAPERONE ACTIVITY OF PEROXIREDOXINS USING IRRADIATION

This patent application is the National Stage of International Application No. PCT/KR2011/007998 filed Oct. 25, 2011, which claims the benefit of priority from Korean Application No. 10-2010-0103847, filed Oct. 25, 2010 and KR-10-2011-0109331 filed Oct. 25, 2011, each of which are herein incorporated by reference in their entirety.

BACKGROUND OF THE INVENTION

1. Field of the Invention

The present invention relates to a method for increasing chaperone activity by irradiating peroxiredoxin proteins.

2. Description of the Related Art

Reactive oxygen species (ROS) is generated during aerobic metabolism or when a living body is exposed on a variety of stress conditions (Finkel T., Curr. Opin. Cell Biol. 15: 247-254, 2003). Such ROS causes serious damages such as oxidative functional impairments or serious structural changes of biological macromolecules (proteins, lipids, nucleic acids, etc.), which can be a cause of various diseases (Neumann et al., Nature, 424: 561-565, 2003). All the aerobic organisms have various forms of molecular chaperones, for example anti-oxidative proteins and heat-shock proteins, in order to protect themselves from protein denaturation and aggregation induced by such protein denaturation mediated by oxidative stress or ROS.

Peroxiredoxin (Prx) has been identified in most eukaryotic cells and prokaryotic cells (Chae et al., J. Biol. Chem., 269: 27670-27678, 1994). Even though peroxiredoxin does not show high homology in total amino acid sequences with the proteins having thioredoxin structure, it is still classified as thioredoxin family (Schroder et al., Protein Sci., 7: 2465-2468, 1998). Prx proteins are divided into two groups according to the number of preserved cysteine (Cys) residues, which are one cysteine Prx (1-Cys Prx) and two cysteine Prx (2-Cys Prx). More particularly, there are 5 groups of Prx proteins according to the number of well-preserved cysteine residues and structural and catalytic characteristics, which are 1-Cys Prx, 2-Cys Prx, type II Prx (Prx II), Prx Q, and GPxs. Among them, 2-Cys Prx has been most studied. It has been known that 2-Cys Prx in *Arabidopsis thaliana* is functioning to protect chloroplast proteins on the surface of stroma of thylakoid membrane of chloroplast from oxidative damage (Baier et al., Plant Phsiol., 199: 1407-1414, 1999). To protect chloroplast from stress induced by ROS, the cysteine residue in 2-Cys Prx active cite is oxidized into sulfenic- or sulfinic form, and the sulfenic form is deoxidized by thioredoxin-h (Trx-h), thioredoxin-f (Trx-f) and thioredoxin-m (Trx-m) (Motohashi et al., Proc. Natl. Acad. Sci., 98: 11224-11229, 2001; Balmer et al., Proc. Natl. Acad. Sci., 100: 370-375, 2003) while the sulfinic form is deoxidized by sulphiredoxin and sestrin (Beteau et al., Nature, 425: 980-984). Prx regulates peroxide mediated signal transduction, according to previous reports. In addition, Prx has many functions involved in cell proliferation, differentiation, immune response, growth regulation, cancer cell development, apoptosis, and many other unidentified functions as well (Neumann et al., Nature, 424: 561-565, 2003; Hirotsu et al., Proc. Natl. Acad. Sci. USA, 96: 12333-12338, 1999).

2-Cys Prx is known to be expressed in various cancers and neurodegenerative diseases such as Alzheimer disease, Pick disease and Down syndrome (Noh, D.Y. et al, Anticancer Res, 2001; Yanagawa, T. et al, Cancer Lett, 1999; Kinnula, V. L. et al, J. Pathol., 2002; Chang, W. J. et al, Biochem. Biophys. Res. Commun., 2001; Multhaup, G. et al, Biochem. Pharmacol, 1997; Krapfenbauer, K. et al, Brain Res., 2003). It is presumed that such expression of 2-Cys Prx is to protect cells from oxidative stress under the cancer and other degenerative disease conditions.

Peroxidase activity is continued by the following cycle: NADPH is converted to NADP$^+$, during which H$^+$ is delivered to thioredoxin reductase (TR); then TR delivers H$^+$ to thioredoxin (Trx) and is oxidized; Trx deoxidized by receiving H$^+$ delivers H$^+$ to Prx, during which Trx is oxidized; and Prx deoxidized by receiving H$^+$ decomposes $H_2O_2$ into $O_2+H_2O$, and this cycle is repeated with the consumption of NADPH (seen FIG. 21).

Chaperone is the protein involved in protein folding. For example, once protein gets stress like heat shock, the original tertiary structure of the protein is denatured, indicating the protein loses its function as a protein. Chaperone protein recognizes the denatured protein and then helps it be folded again.

Molecular chaperone activity is largely divided into holdase activity and foldase activity. Holdase activity is working in the following processes: Once a protein is denatured by the exposure on stress (oxidative stress or heat shock stress), some hydrophobic amino acid residues are exposed and denatured protein fragments are aggregated irregularly to make aggregates. These aggregates are decomposed by protease and at this time chaperone protein (SHSPs, DnaJ) is conjugated to some of the denatured hydrophobic amino acids to inhibit the aggregation and thus to make the protein come back to the original tertiary structure (see FIG. 22).

In the meantime, foldase activity is working in the following processes; once a new protein is synthesized by ribosomes using mRNA as a template, protein folding is induced to allow the protein to have its original tertiary structure. At this time, chaperone protein (GroEL/ES, DnaK/J/E) is conjugated to the newly extended amino acid chain to form the authentic tertiary structure (see FIG. 23).

It has been well-known that 2-Cys Prx protein has double enzyme activities of peroxidase and chaperone protein. It is also known fact that additional cysteine, in addition to the above two cysteines, affects structural change of Prx protein. In particular, Prx PP1084 protein identified from *Pseudomonas putida* (KT2440) by the present inventors is a kind of 2-Cys Prx having double enzyme activities. The protein has strong chaperone activity and forms comparatively high molecular structure. There is an additional cysteine between the two active cysteines and the structural change caused by that cysteine affects the strong chaperone activity.

The present inventors tried to increase chaperone activity of peroxiredoxin proteins (2-Cys and 3-Cys). As a result, the inventors confirmed that Prx protein was depolymerized, dityrosine-bond was increased, beta-sheet and random coil of 2-Cys Prx were increased, alpha helix and turn structure were decreased, and secondary structure was not observed in 3-Cys Prx protein after gamma ray irradiation. The above confirmation supported the new prospect provided by the present inventors on the structural change of a protein in relation to chaperone activity increase. The structural change of Prx induces the increase of hydrophobicity involved in chaperone activity. The present inventor completed this invention by confirming more specifically that chaperone activity of Prx protein was at least three times increased by irradiation with 15~30 kGy of gamma ray, compared with the non-irradiated group, at which chaperone activity was optimized.

SUMMARY OF THE INVENTION

It is an object of the present invention to provide a method to increase chaperone activity of peroxiredoxin (Prx) protein.

It is another object of the present invention to provide Prx protein with increased chaperone activity prepared by the method of the invention and a use of the same.

To achieve the above objects, the present invention provides a method to increase chaperone activity by irradiating Prx.

The present invention also provides Prx with increased chaperone activity by irradiation.

The present invention also provides a composition for enhancing resistance against environmental stress which comprises Prx with increased chaperone activity as an active ingredient.

In addition, the present invention provides a use of Prx with increased chaperone activity by irradiation as a composition for enhancing resistance against environmental stress.

Advantageous Effect

As explained hereinbefore, the method of the present invention to increase chaperone activity by irradiating Prx protein with gamma ray confirmed that the chaperone activity became optimized by irradiation with gamma ray. Such increase of the chaperone activity was also confirmed to be related to the structural change of Prx protein. In 2-Cys Prx, generally known alpha-helix structure was decreased but beta-sheet structure was increased. On the contrary, in 3-Cys Prx, secondary structure of the protein was not observed. The above results brought novel insight on the protein structural change in relation to the increase of chaperone activity. In conclusion, the Prx protein with increased chaperone activity of the present invention enhances resistance against environmental stress, so that it can be effectively used to increase productivity of various organisms including agricultural crops and for industrial mass-production of effective components.

BRIEF DESCRIPTION OF THE DRAWINGS

The application of the preferred embodiments of the present invention is best understood with reference to the accompanying drawings, wherein:

FIG. 1 is a diagram illustrating the subcloning of PP1084 (3-Cys) gene into the expression vector pRSETa:

M: marker; and

12~15: pRSETa::PP1084 (3-Cys).

FIG. 2 is a diagram illustrating the subcloning of PA3529 (2-Cys) gene into the expression vector pRSETa:

M: marker; and

1~5: pRSETa::PA3529 (2-Cys).

FIG. 3 is a diagram confirming the expression of PP1084 protein in *E. Coli* (KRX):

M: marker;

C: the control group wherein PP1084 protein was not over-expressed; and

1~11: PP1084 transformants wherein PP1084 protein was over-expressed by adding 0.2% L-rhamnose.

FIG. 4 is a diagram confirming the expression of PA3529 protein in *E. Coli* (KRX):

M: marker; and

1~5: PA3529 transformants wherein PA3529 protein was over-expressed by adding 0.2% L-rhamnose.

FIG. 5 is a diagram illustrating the fractions obtained through the purification of PP1084 protein:

M: marker;

1: fraction 1;

2: fraction 2; and

3: fraction 3.

FIG. 6 is a diagram illustrating the structural changes of PP1084 protein induced by irradiation with gamma ray, confirmed by loading on polyacrylamide gel:

M: marker;

1: the group irradiated with 0 kGy of gamma ray;

2: the group irradiated with 5 kGy of gamma ray;

3: the group irradiated with 15 kGy of gamma ray;

4: the group irradiated with 30 kGy of gamma ray;

5: the group irradiated with 50 kGy of gamma ray;

6: the group irradiated with 100 kGy of gamma ray;

7: the group irradiated with 200 kGy of gamma ray;

8: the group irradiated with 300 kGy of gamma ray;

9: the group irradiated with 400 kGy of gamma ray; and

10: the group irradiated with 500 kGy of gamma ray;

FIG. 7 is a diagram illustrating the structural changes of PA3529 protein induced by irradiation with gamma ray, confirmed by loading on polyacrylamide gel M: marker;

1: the group irradiated with 0 kGy of gamma ray;

2: the group irradiated with 5 kGy of gamma ray;

3: the group irradiated with 15 kGy of gamma ray;

4: the group irradiated with 30 kGy of gamma ray;

5: the group irradiated with 50 kGy of gamma ray;

6: the group irradiated with 100 kGy of gamma ray;

7: the group irradiated with 200 kGy of gamma ray;

8: the group irradiated with 300 kGy of gamma ray;

9: the group irradiated with 400 kGy of gamma ray; and

10: the group irradiated with 500 kGy of gamma ray;

FIG. 8 is a diagram illustrating the changes of chaperone activity of PP1084 protein over the doses of gamma irradiation.

FIG. 9 is a diagram illustrating the changes of chaperone activity of PA3529 protein over the doses of gamma irradiation.

FIG. 10 is a diagram illustrating the structural changes of PP1084 protein by high dose gamma irradiation, confirmed by FPLC.

FIG. 11 is a diagram illustrating the structural changes of PA3529 protein by high dose gamma irradiation, confirmed by FPLC.

FIG. 12 is a diagram illustrating the partial structural changes of PP1084 protein induced by high dose gamma irradiation.

FIG. 13 is a diagram illustrating the partial structural changes of PA3529 protein induced by high dose gamma irradiation.

FIG. 14 is a diagram illustrating the increase of dityrosine-bond of PP1084 protein induced by high dose gamma irradiation.

FIG. 15 is a diagram illustrating the changes of hydrophobicity of PP1084 protein induced by high dose irradiation.

FIG. 16 is a diagram illustrating the changes of hydrophobicity of PA3529 protein induced by high dose irradiation.

FIG. 17 is a graph illustrating the changes in the secondary structure of PP1084 protein induced by high dose irradiation.

FIG. 18 is a graph illustrating the changes in the secondary structure of PA3529 protein induced by high dose irradiation.

FIG. 19 is a graph illustrating the increase of chaperone activity of PA3529 protein induced by UV irradiation.

FIG. 20 is a graph illustrating the decrease of thioredoxin peroxidase activity of PA3529 protein induced by UV irradiation.

FIG. 21 is a diagram illustrating the Peroxidase activity.
FIG. 22 is a diagram illustrating the Holdase activity.
FIG. 23 is a diagram illustrating the Foldase activity.

DESCRIPTION OF THE PREFERRED EMBODIMENTS

Hereinafter, the present invention is described in detail.

The present invention provides a method to increase chaperone activity of peroxiredoxin protein by irradiation.

In this method to increase chaperone activity, the peroxiredoxin protein is preferably 2-Cys Prx or 3-Cys Prx, but not always limited thereto. The said 2-Cys Prx protein has preferably the amino acid sequence represented by SEQ. ID. NO: 1, but not always limited thereto, and the 3-Cys Prx protein has preferably the amino acid sequence represented by SEQ. ID. NO: 2, but not always limited thereto.

The radiation irradiated to increase chaperone activity herein is preferably selected from the group consisting of gamma ray, electron beam (beta ray), X ray, and UV ray, and more preferably is gamma ray or UV ray, but not always limited thereto. The dose of gamma ray irradiated to increase chaperone activity is preferably 1~500 kGy, and more preferably 2~100 kGy, and most preferably 15~30 kGy, but not always limited thereto. The dose of electron beam irradiated to increase chaperone activity is preferably 1~30 kGy, and more preferably 15~30 kGy, but not always limited thereto. In addition, the dose of UV ray irradiated to increase chaperone activity is preferably 5~240 W, but not always limited thereto.

In a preferred embodiment of the present invention, PP1084 (3-Cys) and PA3529 (2-Cys) genes of *Pseudomonas aeruginosa* PAO1 and *Pseudomonas putida* KT2440 were cloned into the expression vector pRSETa. Then, protein was produced by using the vector, followed by purification (see FIG. 1~FIG. 5). The purified two kinds of Prx proteins (PP1084 and PA3529) were irradiated with gamma ray at 0~500 kGy. The dose of gamma ray that changed the protein structure was investigated. As a result, the destruction of the structure was observed in both Prx proteins irradiated with higher than 100 kGy of gamma ray (see FIG. 6 and FIG. 7).

In a preferred embodiment of the present invention, the effect of gamma irradiation on the purified two kinds of Prx proteins was examined, followed by the investigation whether or not the chaperone activity therein was increased by gamma irradiation. As a result, when gamma ray was irradiated at 30 kGy, chaperone activities of both PP1084 and PA3529 were most increased (see FIG. 8 and FIG. 9). To investigate whether or not the increased chaperone activity was related to the structural change of Prx protein, the structures of two kinds of Prx proteins irradiated with gamma ray were analyzed by FPLC. As a result, PP1084 (3-Cys) and PA3529 (2-Cys) were depolymerized with forming the high molecular weight protein group and the low molecular weight protein group (see FIG. 10 and FIG. 11).

In a preferred embodiment of the present invention, the structural changes in Prx protein induced by high dose gamma irradiation were investigated. The irradiated Prx protein was separated by SDS-PAGE in the reducing environment. As a result, the molecular weight of the Prx protein not irradiated with gamma ray was 25 kDa, while the Prx protein irradiated with gamma ray produced new covalent bonds which would not be reduced by a reducing agent. To confirm the newly formed covalent bond, dityrosine-bond known to be generated under the oxidation state was investigated in PP1084 protein irradiated with gamma ray. As a result, tyrosine bond was increased by gamma irradiation at 30 kGy and 50 kGy (see FIGS. 12~14).

In a preferred embodiment of the present invention, the changes of hydrophobicity of the protein by gamma irradiation that could affect chaperone activity was investigated. As a result, hydrophobicity was increased in PP1084 and PA3529 by gamma irradiation at 30 kGy which was the dose that could increase chaperone activity most (see FIG. 15 and FIG. 16).

In a preferred embodiment of the present invention, the secondary structure changes of Prx protein induced by gamma irradiation were investigated. In general, when chaperone activity was increased, beta-sheet was increased but alpha-helix was decreased in 2-Cys PA3529. However, in 3-Cys PP1084, the secondary structure changes were not observed (see FIG. 17 and FIG. 18).

In a preferred embodiment of the present invention, it was investigated whether or not chaperone activity was increased by UV irradiation. Particularly, after UV irradiation, chaperone activity and thioredoxin peroxidase activity were measured. As a result, as UV irradiation time increased, molecular chaperone activity was increased regularly, but thioredoxin peroxidase activity was decreased (see FIG. 19 and FIG. 20).

Therefore, it was confirmed in this invention that the chaperone activity of Prx protein was significantly increased by irradiation, compared with the group not-irradiated, indicating that irradiation can be effectively used to increase chaperone activity of peroxiredoxin.

Peroxiredoxin protein was depolymerized by gamma irradiation, and at this time dityrosine-bond was increased, beta-sheet and random coil were increased in the secondary structure of 2-Cys Prx protein, but alpha-helix and turn structure were decreased. In the meantime, the secondary structure changes were not observed in 3-Cys Prx protein. That is, the structural changes in protein in relation to chaperone activity were new discovery. Such structural changes in peroxiredoxin protein induce the increase of hydrophobicity in relation to chaperone activity. Chaperone activity of Prx protein was three-fold increased by gamma irradiation at 15~30 kGy, compared with the non-irradiated group, indicating the chaperone activity became optimized. It was also confirmed that chaperone activity of 2-Cys Prx protein was significantly increased by UV irradiation as well, in addition to gamma irradiation, compared with the non-irradiated group.

Therefore, the method of irradiation of the present invention can be effectively used for the method to increase chaperone activity of Prx protein.

The present invention also provides peroxiredoxin protein with increased chaperone activity by irradiation.

In this invention, the peroxiredoxin protein is preferably 2-Cys Prx or 3-Cys Prx, but not always limited thereto. The said 2-Cys Prx protein has the amino acid sequence represented by SEQ. ID. NO: 1, but not always limited thereto, and the said 3-Cys Prx protein has the amino acid sequence represented by SEQ. ID. NO: 2, but not always limited thereto.

In this invention the radiation is preferably selected from the group consisting of gamma ray, electron beam (beta ray), X ray, and UV ray, and more preferably is gamma ray or UV ray, but not always limited thereto. The dose of gamma ray irradiated to increase chaperone activity is preferably 1~500 kGy, and more preferably 2~100 kGy, and most preferably 15~30 kGy, but not always limited thereto. The dose of electron beam irradiated to increase chaperone activity is preferably 1~30 kGy, and more preferably 15~30 kGy, but not always limited thereto. In addition, the dose of UV ray irradiated to increase chaperone activity is preferably 5~240 W, but not always limited thereto.

In a preferred embodiment of the present invention, it was observed that chaperone activity of peroxiredoxin was increased by irradiation with gamma ray or UV. Particularly, when 15~30 kGy of gamma ray was irradiated to peroxiredoxin, the protein was depolymerized, and at this time the structural change such as the increase of dityrosine-bond was observed as well. Such structural change induced the increase of hydrophobicity of the protein, and accordingly increased chaperone activity at least three times as high as that of the non-irradiated control group. Chaperone activity of 2-Cys Prx was significantly increased by UV irradiation, in addition to gamma irradiation, compared with the non-irradiated group.

Therefore, the method using irradiation of the present invention can be effectively applied to produce the peroxiredoxin protein with increased chaperone activity.

The present invention also provides a composition for enhancing resistance against environmental stress which comprises the peroxiredoxin with increased chaperone activity of the invention as an active ingredient.

In addition, the present invention provides a use of the peroxiredoxin with increased chaperone activity of the invention as the composition for enhancing resistance against environmental stress.

In a preferred embodiment of the present invention, it was observed that chaperone activity of peroxiredoxin was increased by irradiation with gamma ray or UV. Particularly, when 15~30 kGy of gamma ray was irradiated to peroxiredoxin, the protein was depolymerized, and at this time the structural change such as the increase of dityrosine-bond was observed as well. Such structural change induced the increase of hydrophobicity of the protein, and accordingly increased chaperone activity at least three times as high as that of the non-irradiated control group. Chaperone activity of 2-Cys Prx was significantly increased by UV irradiation, in addition to gamma irradiation, compared with the non-irradiated group.

Therefore, the peroxiredoxin with increased chaperone activity prepared by irradiation of the invention was confirmed to increase resistance against environmental stress, indicating that it can be effectively used as a composition for enhancing resistance against environmental stress.

Practical and presently preferred embodiments of the present invention are illustrative as shown in the following Examples, Experimental Examples and Manufacturing Examples.

However, it will be appreciated that those skilled in the art, on consideration of this disclosure, may make modifications and improvements within the spirit and scope of the present invention.

Example 1

Preparation of Peroxiredoxin Proteins (PP1084, PA3529)

<1-1> Cloning of Peroxiredoxin (PRX) Gene

PRXgene was obtained from each genomic DNA of *Pseudomonas aeruginosa* PAO1 and *Pseudomonas putida* KT2440 by polymerase chain reaction (PCR) and then cloned into pGEMT-easy vector, followed by sequencing analysis to confirm the gene. The gene was sub-cloned into the restriction enzyme site of multi-cloning site of the expression vector pRSETa.

Particularly, PCR was performed as follows for the cloning of PP1084 gene. 10 ng of *Pseudomonas aeruginosa* PAO1 or *Pseudomonas putida* KT2440 genomic DNA, 0.2 uM dNTP, 20 pmol of a forward primer, 20 pmol of a reverse primer, 1 unit of Taq polymerase, and distilled water were mixed to make the final volume 20 µl. All the PCRs were performed as follows; predenaturation at 94° C. for 1 minute, denaturation at 94° C. for 30 seconds, annealing at 50° C. for 30 seconds, extension at 72° C. for 45 minutes, 35 cycles from denaturation to extension, and final extension at 72° C. for 10 minutes. The primers used for PCR were as follows:

```
Pseudomonas aeruginosa PAO1 forward primer:
                                  (SEQ. ID. NO: 3)
5'-ccgctcgagatgagcgtactc-3';

Pseudomonas aeruginosa PAO1 reverse primer:
                                  (SEQ. ID. NO: 4)
3'-cgagctcttacagcttgccagc-5';

Pseudomonas putida KT2440 forward primer:
                                  (SEQ. ID. NO: 5)
5'-ccgctcgagatgagcgtactcgta-3';
and Pseudomonas putida KT2440 reverse primer:
                                  (SEQ. ID. NO: 6)
3'-cccaagcttttacagcttgctggc-5'.
```

*Pseudomonas aeruginosa* PA01 genomic DNA proceeded to PCR using the primers represented by SEQ. ID. NO: 3 and SEQ. ID. NO: 4 containing XhoI and ScaI sites, and *Pseudomonas putida* KT2440 genomic DNA proceeded to PCR using the primers represented by SEQ. ID. NO: 5 and SEQ. ID. NO: 6 containing XhoI and HindIII sites. The obtained two kinds of PRX genes were inserted in the cloning vector pGEMT-easy, followed by sequencing analysis to confirm the nucleotide sequence of each gene above. Each gene was sub-cloned into the restriction enzyme site of multi-cloning site of the expression vector pRSETa.

To induce the expression and purification of Prx protein from the PP1084 gene inserted in the expression vector pRSETa, *E. coli* (KRX strain; Promega, USA) was transformed with the vector. The Prx protein inserted in pRSETa was over-expressed by using T7 promoter. To purify and isolate Prx protein easily, 6 histidines (His) were conjugated to N-terminal of Prx protein, leading to the synthesis of the protein. To operate T7 promoter of pRSETa vector, T7 RNA polymerase was supplied to the host *E. coli* cells. The KRX strain was the host *E. coli* in which T7 polymerase supply was regulated by L-rhamnose. To purify Prx protein, PP1084 transformant clone was prepared, to which numbers (1~11) were assigned (FIG. 1). PA3529 transformant clone was also prepared, to which numbers (1~5) were assigned (FIG. 2).

PP1084 clone and PA3529 clone were seeded in 15 Ml test-tube containing 5 Ml of LB (Luria-Bertani) medium at the ratio of 1:100, followed by culture at 30° C., 120 rpm. The culture continued until $OD_{600nm}$ reached 0.4. Then, 20% L-rhamnose was added thereto (final conc.: 0.2%), followed by culture at 37° C., 120 rpm for 2 hours. The cells induced by 1 Ml of L-rhamnose were obtained by centrifugation at 4° C., 6000 rpm for 10 minutes, to which 100 µl of 1× gel loading buffer was added, followed by resuspending and boiling at 100° C. for 5 minutes. Each sample prepared above was loaded on SDS-PAGE gel by 7 µl, followed by electrophoresis to confirm the over-expression of PP1084 and PA3529 (FIG. 3 and FIG. 4).

<1-2> Purification of PRX Protein

To mass-produce the two kinds of PRX genes cloned in the expression vector pRSETa, each gene prepared in Example <1-1> was over-expressed by using *E. coli* system. PP1084 clone and PA3529 clone were seeded in 2 l Erlenmeyer flask containing 400 Ml of LB (Luria-Bertani) medium at the ratio of 1/100, followed by culture at 30° C., 120 rpm. The culture continued until OD$_{600nm}$ reached 0.4. Then, 20% L-rhamnose was added thereto (final conc.: 0.2%), followed by culture at 30° C., 120 rpm. The cells induced by L-rhamnose were obtained by centrifugation at 4° C., 6000 rpm, for 10 minutes. The obtained cells were suspended in binding buffer [20 mM Tris-HCl (pH 7.5), 0.5 M NaCl, 5 mM Imidazole] containing 0.02% triton X-100, which was then kept frozen. At this time, 30 Ml of the binding buffer was added to 400 Ml of LB. The cells were lysed by using sonicator. The cell lysate was centrifuged at 4° C., 15000 rpm, for 40 minutes to separate supernatant. The cell lysate was added to pre-equilibrated NTA-chelate resin (Peptron, Daejeon, Korea), followed by shaking in rotating wheel at 4° C. for at least one hour to induce binding of the cells to resin. Upon completion of the shaking, centrifugation was performed at 4° C., 1000 rpm, for 5 minutes to separate resin and supernatant respectively. Washing buffer [20 mM Tris-HCl (pH 7.5), 0.5 M NaCl, 50 mM Imidazole] was added to the separated resin at the amount of 5 times the volume of the resin, followed by shaking in rotating wheel at 4° C. for at least one hour to eliminate the supernatant. The said process was repeated 5 times. Elution buffer [20 mM Tris-HCl (pH 7.5), 0.5 M NaCl, 200~400 mM Imidazole] was added to the resin at the amount of 0.5~1 times the volume of the resin, followed by shaking in rotating wheel at 4° C. for at least one hour to obtain supernatant. This process was repeated three times. Then, the obtained supernatant was classified as elution fraction 1, elution fraction 2, and elution fraction 3, and stored. The elution fraction was transferred into membrane tube, followed by dialysis by using 1 L of 50 mM Hepes (pH 8.0) three times, and then the buffer was replaced with fresh one. Concentration was performed with centricon and the concentrate was stored at −80° C. until use.

<1-3> Confirmation of purified Prx protein by SDS-PAGE

To confirm the concentrated protein by using centricon, the purity and concentration of the concentrated Prx protein were measured by SDS-PAGE (FIG. 5).

As a result, as shown in FIG. 5, Prx protein was detected at the size of 25 kDa, confirmed by Western blotting with the elution fractions 1, 2, and (FIG. 5).

Example 2

Screening of Gamma Ray Dose for Inducing Structural Changes of Prx Proteins (2-Cys, 3-Cys) and for Increasing Chaperone Activity The concentrations of the two Prx proteins isolated and purified in Example 1 were adjusted to 1 mg/Ml. 1 Ml of each protein was distributed in Eppendorf tube, which was irradiated with high dose gamma ray (0~500 kGy). For the high dose gamma irradiation, $^{60}$Co gamma ray irradiator ($^{60}$Co, ca. 150 TBq capacity; Atomic Energy of Canada Limited, Canada) in Advanced Radiation Technology Institute of Korea Atomic Energy Research Institute (KAER1) was used. Gamma ray was irradiated at 0, 2, 5, 15, 30, 50, 100, 200, 300, 400, and 500 kGy respectively.

After gamma irradiation, structural changes of the protein were analyzed by using poly-acrylamide gel. Particularly, non-reducing PAGE and native-PAGE were used. Non-reducing PAGE is the method to analyze protein structure in non-reducing form, which can only confirm the structure supported by disulfide bond. Native-PAGE is the method to analyze protein structure formed by covalent bond and non-covalent bond. After gamma irradiation respectively at 0, 2, 5, 15, 30, 50, 100, 200, 300, 400, and 500 kGy, equal amount of the protein was electrophoresed, followed by staining with Coomassie brilliant blue-R-250 to investigate the structural changes of the protein.

As a result, as shown in FIG. 6, it was confirmed by non-reducing PAGE and native PAGE that the band generated by PP1084 protein irradiated with 5 kGy of gamma ray was darker than the band generated by the protein non-irradiated (lane 1). When the protein was irradiated with gamma ray higher than 100 kGy, protein band was not observed. This result indicated that the protein structure was destroyed by gamma irradiation, resulting in depolymerization. As shown in FIG. 7, PA3529 also produced darker band when irradiated with 5~50 kGy of gamma ray, compared with the band in lane 1 which was not irradiated, and then the strength had been reduced since. Like PP1084 protein, when PA3529 was irradiated with gamma ray higher than 100 kGy, protein band was not observed, indicating that protein structure was destroyed by gamma irradiation (FIG. 6 and FIG. 7).

Example 3

Chaperone Activity of Prx Protein (2-Cys, 3-Cys)

It is generally known that when a protein is exposed on stress (oxidative stress, heat stress, etc.), it is denatured and accordingly the folded tertiary structure of the protein gets loosened and hydrophobic amino acid residues are exposed. As the said phenomenon repeats and gets worse, the denatured proteins turn into irregular aggregates which are decomposed by protease. At this time, chaperone protein (for example, sHSPs, DnaJ, etc.) is bound to hydrophobic amino acids of the protein unfolded by stress, to prevent the protein from being aggregates and to make the environment appropriate for the protein to turn back to the original tertiary structure.

Molecular chaperone activity is divided into holdase activity and foldase activity. In this example, holdase activity was analyzed. The analysis of holdase activity was performed based on the following ideas. If malate dehydrogenase (MDH) that is sensitive to heat stress is heated at 43° C., MDH will be denatured to become aggregates. OD$_{650nm}$ will be increased over the heating time by MDH denaturation. However, if MDH is heated in the presence of the protein having chaperone activity, denaturation of MDH will be inhibited, so that OD will not be increased.

Particularly, while MDH protein alone was heated at 43° C., increase rate of OD$_{650nm}$ was measured. Peroxiredoxin protein was added to MDH protein at different ratios, which was heated at 43° C., during which increase rate of OD$_{650nm}$ was measured. The experiment was performed under the conditions as described in Table 1 and Table 2.

TABLE 1

Conditions for measuring chaperone activity of PP1085

| | MDH (Control) | 0 kGy (1:0.3) | 0 kGy (1:1) | 15 kGy (1:0.3) | 30 kGy (1:0.3) | 50 kGy (1:0.3) | 100 kGy (1:0.3) | 300 kGy (1:0.3) | 500 kGy (1:0.3) |
|---|---|---|---|---|---|---|---|---|---|
| MDH | 6.5 μl | 6.5 μl | 6.5 μl | 6.5 μl | 6.5 μl | 6.5 μl | 6.5 μl | 6.5 μl | 6.5 μl |
| 1M hepes (pH 8.0) | 15 μl | 15 μl | 15 μl | 15 μl | 15 μl | 15 μl | 15 μl | 15 μl | 15 μl |
| PP1084 | 0 | 3 μl | 10 μl | 3 μl | 3 μl | 3 μl | 3 μl | 3 μl | 3 μl |
| DW | 278.5 μl | 275.5 μl | 268.5 μl | 275.5 μl | 275.5 μl | 275.5 μl | 275.5 μl | 275.5 μl | 275.5 μl |
| Total | 300 μl | 300 μl | 300 μl | 300 μl | 300 μl | 300 μl | 300 μl | 300 μl | 300 μl |

TABLE 2

Conditions for measuring chaperone activity of PA3529

| | MDH (Control) | 0 kGy (1:5) | 5 kGy (1:5) | 15 kGy (1:5) | 30 kGy (1:5) | 50 kGy (1:5) | 100 kGy (1:5) | 300 kGy (1:5) | 500 kGy (1:5) |
|---|---|---|---|---|---|---|---|---|---|
| MDH | 6.5 μl | 6.5 μl | 6.5 μl | 6.5 μl | 6.5 μl | 6.5 μl | 6.5 μl | 6.5 μl | 6.5 μl |
| 1M hepes (pH 8.0) | 15 μl | 15 μl | 15 μl | 15 μl | 15 μl | 15 μl | 15 μl | 15 μl | 15 μl |
| PP1084 | 0 | 50 μl | 50 μl | 50 μl | 50 μl | 50 μl | 50 μl | 50 μl | 50 μl |
| DW | 278.5 μl | 228.5 μl | 228.5 μl | 228.5 μl | 228.5 μl | 228.5 μl | 228.5 μl | 228.5 μl | 228.5 μl |
| Total | 300 μl | 300 μl | 300 μl | 300 μl | 300 μl | 300 μl | 300 μl | 300 μl | 300 μl |

As shown in FIG. 8 and FIG. 9, PP1084 protein having 3-Cys and PA3529 protein having 2-Cys were irradiated with gamma ray at 0, 5, 15, 30, 50, 100, 300, and 500 kGy, followed by measuring OD. As a result, the lowest OD was observed at 30 kGy, indicating that chaperone activity was highest at 30 kGy (FIG. 8 and FIG. 9).

Example 4

Analysis of Structural Changes of Prx Protein Induced by High Dose Gamma Irradiation To analyze the structural changes of Prx proteins (PP1084 and PA3529) induced by high dose gamma irradiation, FPLC (AKTA; Amersham Biosciences) was used. Prx protein and 50 mM Hepes buffer (pH 8.0) were passed through superdex 200 HR 10/30 column (flow rate: 0.5 Ml/min). Then, chromatogram was made with protein peak measured at $OD_{280nm}$.

As a result, two Prx proteins (PP1084 and PA3529) formed two different protein groups, the high molecular protein group that passed through the column at the time point of 15~20 minutes (F-1) and the low molecular protein group that passed through the column at the time point of 20~25 minutes (F-2). Even though chaperone activity was increased after the high dose gamma irradiation, high molecular structures of the two Prx proteins (PP1084 and PA3529) turned into low molecular structures (depolymerization) by the gamma irradiation (FIG. 10 and FIG. 11).

Example 5

Generation of New Covalent Bonds in Prx Protein by High Dose Gamma Irradiation

The concentrations of the two Prx proteins isolated and purified in Example 1 were adjusted to 1 mg/Ml. 1 Ml of each protein was distributed in Eppendorf tube, which was irradiated with high dose gamma ray (0~500 kGy). For the high dose gamma irradiation, $^{60}$Co gamma ray irradiator ($^{60}$Co, ca. 150 TBq capacity; Atomic Energy of Canada Limited, Canada) in Advanced Radiation Technology Institute of Korea Atomic Energy Research Institute (KAERI) was used. Gamma ray was irradiated at the dose of 0~500 kGy. To investigate the structural changes of the high dose gamma irradiated protein, SDS-PAGE was performed under the completely reduced environment. Equal amount of the protein was electrophoresed, followed by staining with Coomassie brilliant blue R-250 to investigate the structural changes of the protein.

As a result, the proteins of the two control groups not irradiated with high dose gamma ray demonstrated approximately 25 kDa of molecular weight, which was the molecular weight of a monomer, in the reducing SDS-PAGE. However, the protein irradiated with gamma ray produced new covalent bond that was not reduced by a reducing agent. According to the previous reports, dityrosine bond formed by tyrosines each other was generated under the strong oxidative stress or the severe oxidation condition. Based on the fact, the present inventors presumed that the newly generated covalent bond herein would be dityrosine bond and the inventors tried to confirm the presumption.

Example 6

Increase of Dityrosine Bond by High Dose Gamma Irradiation

The concentrations of the two Prx proteins isolated and purified in Example 1 were adjusted to 1 mg/Ml. 1 Ml of each protein was distributed in Eppendorf tube, which was irradiated with high dose gamma ray (0~500 kGy). For the high dose gamma irradiation, $^{60}$Co gamma ray irradiator ($^{60}$Co, ca. 150 TBq capacity; Atomic Energy of Canada Limited, Canada) in Advanced Radiation Technology Institute of Korea Atomic Energy Research Institute (KAERI) was used.

Gamma ray was irradiated at the dose of 0~500 kGy. To confirm the increase of dityrosine bond generated by high dose gamma irradiation, SDS-PAGE was performed under the completely reduced environment. Dityrosine bond was selectively obtained by using anti-dityrosine anti-body from the protein separated by SDS-PAGE, followed by imaging.

Particularly, PP1084 protein was irradiated with high dose gamma ray at different levels, followed by SDS-PAGE electrophoresis. Each of PP1084 protein separated by SDS-PAGE according to molecular weight was transferred onto NC membrane (nitrocellulose membrane; Bio-rad, USA). Blocking was performed with 5% skim milk for 1 hour, followed by washing the membrane with T-TBS buffer [10 mM Tris-HCl (pH 7.5), 150 mM NaCl, 0.05% tween-20] once for 10 minutes. The membrane was reacted with anti-dityrosine antibody diluted in T-TBS buffer (5000:1) for 1 hour, followed by washing with shaking strongly with T-TBS buffer for 2 minutes, 5 times. PP1084 protein formed anti-dityrosine antibody conjugated dityrosine bond was selectively detected by using HRP detection kit.

As a result, as shown in FIG. 12 and FIG. 13, the reduced PP1084 and PA3529 proteins were confirmed to be in the monomer size of 25 kDa (1:0 kGy of FIG. 12 and FIG. 13). Those two Prx proteins demonstrated structural changes induced by high dose gamma irradiation. Particularly, compared with the gamma ray non-irradiated group, the Prx proteins irradiated with 2~50 kGy of gamma ray demonstrated structural changes most apparently at 50 kDa (FIG. 12 and FIG. 13). To investigate whether such structural change in Prx protein was attributed to dityrosine bond, the changes of dityrosine bond were measured by using anti-tyrosine antibody. As a result, dityrosine bond in 50 kDa size PP1084 protein irradiated with 30~50 kGy of gamma ray was significantly increased, compared with the gamma ray non-irradiated group (FIG. 14).

Example 7

Changes of Hydrophobicity of Prx Protein Induced by High Dose Gamma Irradiation

Prx protein maintains its water-solubility by locating its hydrophilic domain outside and hydrophobic domain inside. However, chaperone protein has been known to have a high rate of hydrophobic domain outside.

It was observed in Examples 2~6 that chaperone activities of the two Prx proteins were increased when they were irradiated with high dose gamma ray (15~30 kGy). Therefore, the present inventors presumed that high dose gamma ray would make hydrophobic domain exposed so that chaperone activity would increase, and thereafter the inventors tried to confirm the presumption.

To confirm the cause of chaperone activity increase, bis-ANS binding test was performed with the composition shown in Table 3 and Table 4 to investigate the hydrophobicity playing an important role in chaperone activity. Particularly, Prx protein was reacted with bis-ANS [1,1'-bi(4-anilino) naphthalene-5,5'-disulfonic acid] at 25° C. for 30 minutes. Then, fluorescence analysis was performed by using SFM25 spectrofluorometer (Kontron, Germany) at 380~600 nm to investigate the exposure of hydrophobic domain of the protein.

TABLE 3

Conditions for analyzing changes of hydrophobicity of PP1085

|  | 0 kGy | 5 kGy | 15 kGy | 30 kGy | 300 kGy |
|---|---|---|---|---|---|
| Bis-ANS (1 mM) | 10 μl | 10 μl | 10 μl | 10 μl | 10 μl |
| 1M Hepes (pH 8.0) | 50 μl | 50 μl | 50 μl | 50 μl | 50 μl |
| PP1084 protein | 100 μg | 100 μg | 100 μg | 100 μg | 100 μg |
| DW | 200 μl | 200 μl | 200 μl | 200 μl | 200 μl |
| Total | 300 μl | 300 μl | 300 μl | 300 μl | 300 μl |

TABLE 4

Conditions for analyzing changes of hydrophobicity of PA3529

|  | 0 kGy | 5 kGy | 15 kGy | 30 kGy | 50 kGy | 300 kGy |
|---|---|---|---|---|---|---|
| Bis-ANS (1 mM) | 10 μl | 10 μl | 10 μl | 10 μl | 10 μl | 10 μl |
| 1M Hepes (pH 8.0) | 50 μl | 50 μl | 50 μl | 50 μl | 50 μl | 50 μl |
| PA3529 protein | 100 μg | 100 μg | 100 μg | 100 μg | 100 μg | 100 μg |
| DW | 200 μl | 200 μl | 200 μl | 200 μl | 200 μl | 200 μl |
| Total | 300 μl | 300 μl | 300 μl | 300 μl | 300 μl | 300 μl |

As a result, as shown in FIG. 15, hydrophobicity of 3-Cys PP1084 protein was increased when the protein was irradiated with 5 kGy gamma ray, compared with the gamma ray non-irradiated control group. However, hydrophobicity of the protein irradiated with higher doses of gamma ray (15, 30, or 300 kGy) was not changed or decreased, compared with the gamma ray non-irradiated control group. In the meantime, as shown in FIG. 16, hydrophobicity of 2-Cys PA3529 protein was increased in all the groups irradiated with gamma ray, compared with the control group. At this time, the increase of hydrophobicity was most apparent at 30 kGy, followed by 50, 15, 5, and 300 kGy in that order (FIG. 15 and FIG. 16)

Example 8

Changes of Secondary Structure of Prx Protein Induced by High Dose Gamma Irradiation It was investigated how high dose gamma ray could affect the secondary structure of Prx protein and whether or not such structural change could induce any change in chaperone activity and structure of Prx protein. To do so, circular dichroism spectroscopy was performed. Particularly, such secondary structures as beta-sheet, turn and ransom coil were observed.

To obtain better result, the buffer for Prx protein was replaced with 10 mM Tris (pH 8.0) buffer and Far UV-CD spectrum (190~250 nm) was analyzed by using Jasco J-715 spectropolarimeter (Jasco, Great Dunmow, UK) to investigate the secondary structure of Prx protein.

As a result, changes of two-dimensional alpha-helix, beta-sheet, turn, and random coil structures in 3-Cys PP1084 protein over the dose of gamma ray were not observed. However, in 2-Cys PA3529 protein, alpha-helix structure was reduced from 56% to 0% but beta-sheet structure was increased from 0 to 56%. Turn structure was reduced from 23.3% to 0% but random coil structure was increased from 19% to 49.6%. That is, the increase of beta-sheet structure and the decrease of alpha-helix structure, indicating the increase of chaperone activity, were observed in 2-Cys PA3529 protein, while no changes of the secondary structures were observed in 3-Cys PP1084 protein despite chaperone activity was increased by gamma ray (FIG. 17 and FIG. 18).

TABLE 5

Conditions for analyzing changes of secondary structure of PP1084 protein

|  | 0 kGy | 2 kGy | 5 kGy | 10 kGy | 15 kGy | 20 kGy | 30 kGy | 50 kGy | 100 kGy | 200 kGy | 300 kGy | 400 kGy | 500 kGy |
|---|---|---|---|---|---|---|---|---|---|---|---|---|---|
| 1M Tris HCl (pH 8.0) | 3 μl | 3 μl | 3 μl | 3 μl | 3 μl | 3 μl | 3 μl | 3 μl | 3 μl | 3 μl | 3 μl | 3 μl | 3 μl |
| PP1084 protein | 100 μg | 100 μg | 100 μg | 100 μg | 100 μg | 100 μg | 100 μg | 100 μg | 100 μg | 100 μg | 100 μg | 100 μg | 100 μg |
| DW | 200 μl | 200 μl | 200 μl | 200 μl | 200 μl | 200 μl | 200 μl | 200 μl | 200 μl | 200 μl | 200 μl | 200 μl | 200 μl |
| Total | 300 μl | 300 μl | 300 μl | 300 μl | 300 μl | 300 μl | 300 μl | 300 μl | 300 μl | 300 μl | 300 μl | 300 μl | 300 μl |

TABLE 6

Conditions for analyzing changes of secondary structure of PA3529 protein

|  | 0 kGy | 2 kGy | 5 kGy | 10 kGy | 15 kGy | 20 kGy | 30 kGy | 50 kGy | 100 kGy | 200 kGy | 300 kGy | 400 kGy | 500 kGy |
|---|---|---|---|---|---|---|---|---|---|---|---|---|---|
| 1M Tris HCl (pH 8.0) | 3 μl | 3 μl | 3 μl | 3 μl | 3 μl | 3 μl | 3 μl | 3 μl | 3 μl | 3 μl | 3 μl | 3 μl | 3 μl |
| PA3529 protein | 100 μg | 100 μg | 100 μg | 100 μg | 100 μg | 100 μg | 100 μg | 100 μg | 100 μg | 100 μg | 100 μg | 100 μg | 100 μg |
| DW | 200 μl | 200 μl | 200 μl | 200 μl | 200 μl | 200 μl | 200 μl | 200 μl | 200 μl | 200 μl | 200 μl | 200 μl | 200 μl |
| Total | 300 μl | 300 μl | 300 μl | 300 μl | 300 μl | 300 μl | 300 μl | 300 μl | 300 μl | 300 μl | 300 μl | 300 μl | 300 μl |

Example 9

Measurement of Chaperone Activity and POD Activity of Prx Protein (2-Cys) Over UV Irradiation To investigate the changes of physiological activities of PaPrx (*Pseudomonas aeruginosa* 3529, PA3529) protein induced by UV irradiation, the protein was UV irradiated at 5 W by using 15-watt medium wave UV lamp (Spectroline, USA) with maintaining the temperature at 4° C. under the darkness. At this time, UV strength was measured by UV digital radiometer #DRC-100X (Spectroline, USA). Each PaPrx protein was irradiated with UV for different lengths of time (0 h~5 h).

<9-1> Measurement of Chaperone Activity

To measure molecular chaperone activity, heat stress (43° C.) was given to the UV irradiated PaPrx protein by using malate dehydrogenase (MDH) as a substrate at 340 nm, and then MDH aggregation was measured for 15 minutes. At this time, the ratio of PaPrx protein to MDH protein for the reaction was 1:1 and OD was measured by using DU800 spectrophotometer (Beckmann, USA) (FIG. 19).

As a result, as the UV irradiation time increased, the molecular chaperone activity increased regularly (FIG. 19).

<9-2> Measurement of Thioredoxin Peroxidase Activity

Thioredoxin peroxidase activity of the UV irradiated PaPrx protein was measured by using Trx system [10 mM NADPH nicotinamide adenine dinucleotide phosphate), 1 uM yeast Trx (yeast thioredoxin), 5 uM TR (thioredoxin reductase), 1 uM PaPrx protein, and 50 mM Hepes]. The reaction was measured by observing oxidation of NADPH by 10 μl of $H_2O_2$ for 10 minutes at 340 nm. At this time, OD was measured by using DU800 spectrophotometer (Beckmann, USA).

As a result, as the UV irradiation time increased, the thioredoxin peroxidase activity was reduced regularly (FIG. 20).

Industrial Applicability

As explained hereinbefore, the peroxiredoxin having chaperone activity increased significantly by UV irradiation demonstrated strong resistance against various environmental stresses including oxidative stress and heat stress. Therefore, the protein and the transformant prepared by using the protein can greatly contribute to the mass-production of active ingredients of agricultural crops and to increase productivity of the same by protecting various organisms including agricultural crops from being damaged by environmental stresses.

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended Claims.

What is claimed is:

1. A method for increasing chaperone activity and increasing dityrosine bond of 2-Cys peroxiredoxin protein having two or three cysteine residues comprising the steps of:
    irradiating the 2-Cys peroxiredoxin protein having two or three cysteine residues with gamma ray radiation, wherein the dose of gamma ray is 5~500 kGy; and
    measuring the chaperone activity of the 2-Cys peroxiredoxin protein having two or three cysteine residues.

2. The method for increasing chaperone activity and increasing dityrosine bond according to claim 1, wherein the peroxiredoxin protein consists of the amino acid sequence of SEQ. ID. NO: 1 or SEQ. ID. NO: 2.

3. The method for increasing chaperone activity and increasing dityrosine bond according to claim 1, wherein the dose of gamma ray is 5~30 kGy.

4. The method for increasing chaperone activity and increasing dityrosine bond according to claim 1, wherein the dose of gamma ray is 5~100 kGy.

* * * * *